(12) United States Patent
Volkman et al.

(10) Patent No.: US 8,524,670 B2
(45) Date of Patent: Sep. 3, 2013

(54) ENGINEERED CXCL12 ALPHA LOCKED DIMER POLYPEPTIDE

(75) Inventors: Brian F. Volkman, Muskego, WI (US); Christopher T. Veldkamp, Milwaukee, WI (US); Francis C. Peterson, Racine, WI (US); Thomas Sakmar, New York, NY (US); Christoph H. Seibert, Frankfurt am Main (DE)

(73) Assignees: Medical College of Wisconsin Research Foundation, Milwaukee, WI (US); The Rockefeller University, New York, NY (US)

( * ) Notice: Subject to any disclaimer, the term of this patent is extended or adjusted under 35 U.S.C. 154(b) by 0 days.

(21) Appl. No.: 12/956,514

(22) Filed: Nov. 30, 2010

(65) Prior Publication Data

US 2011/0091410 A1    Apr. 21, 2011

Related U.S. Application Data

(63) Continuation of application No. 12/380,308, filed on Feb. 26, 2009, now Pat. No. 7,923,016.

(60) Provisional application No. 61/067,723, filed on Mar. 1, 2008.

(51) Int. Cl.
*A61K 38/00*    (2006.01)

(52) U.S. Cl.
USPC ....... 514/19.3; 514/18.9; 514/19.6; 514/19.8; 514/1.1

(58) Field of Classification Search
None
See application file for complete search history.

(56) References Cited

U.S. PATENT DOCUMENTS 6,875,738 B1    4/2005    Clark-Lewis et al.

OTHER PUBLICATIONS

Leukemia, http://medical-dictionary.thefreedictionary.com/leukemia; accessed Apr. 25, 2012.*
O'Connor (2005, Eur. J. Haematol. Suppl. 66 75:150-158).*
Schwartz et al. (2008, J. Manag. Care Pharm. 14 Suppl S: S12-S18).*
Tanaka et al. (2012, Expert Opin. Pharmacol. 13:815-828).*
Veldkamp et al., "Recognition of a CXCR4 sulfotyrosine by the chemokine stromal cell-derived factor-1alpha (SDF-1alpha/CXCL12)", J. Mol. Biol., 2006; 359:1400-1409.
Veldkamp et al., "Structural basis of CXCR4 sulfotyrosine recognition by the chemokine SDF-1/CXCL12", Sci. Signal., 2008; 1:ra4.
Fernando et al., "Thermodynamic characterization of interleukin-8 monomer binding to CXCR1 receptor N-terminal domain", FEBS J., 2007; 274:241-251.
Jin et al., The human CC chemokine MIP-1beta dimer is not competent to bind to the CCR5 receptor, J. Biol. Chem., 2007; 282:27976-27983.
Zlotnik et al., "Chemokines and cancer", Int. J. Cancer, 2006; 119:2026-2029.
Rajarathnam et al., "Probing receptor binding activity of interleukin-8 dimer using a disulfide trap", Biochemistry, 2006; 45:7882-7888.
Veldkamp et al., "The monomer-dimer equilibrium of stromal cell-derived factor-1 (CXCL 12) is altered by pH, phosphate, sulfate, and heparin", Protein Sci., 2005; 14:1071-1081.

(Continued)

*Primary Examiner* — Elizabeth C Kemmerer
(74) *Attorney, Agent, or Firm* — Quarles & Brady LLP

(57) ABSTRACT

The present invention provides a novel CXCL12-$\alpha_2$ locked dimer polypeptide, pharmaceutical compositions thereof, and methods of using said dimer in the treatment of cancer, inflammatory disorders, autoimmune disease, and HIV/AIDS.

7 Claims, 20 Drawing Sheets

A

(56) References Cited

OTHER PUBLICATIONS

Proudfoot et al., "Glycosaminoglycan binding and oligomerization are essential for the in vivo activity of certain chemokines", Proc. Natl. Acad. Sci. U.S.A., 2003; 100:1885-1890.

Muller et al, "Involvement of chemokine receptors in breast cancer metastasis", Nature, 2001; 410:50-56.

Loetscher et al., "N-terminal peptides of stromal cell-derived factor-1 with CXC chemokine receptor 4 agonist and antagonist activities", J. Biol. Chem., 1998; 273:22279-22283.

Crump et al., "Solution structure and basis for functional activity of stromal cell-derived factor-1; dissociation of CXCR4 activation from binding and inhibition of HIV-1", EMBO J., 1997; 16:6996-7007.

Vianello et al., "Fugetaxis: active movement of leukocytes away from a chemokinetic agent", J. Mol. Med., 2005; 83:752-763.

Byrne et al., Chemically crosslinked protein dimers: stability and denaturation effects, Protein Science, 1995, 4:2545-2558.

PCT International Search Report, PCT/US2009/035318, Jul. 14, 2009.

United States Patent and Trademark Office, Office Action, U.S. Appl. No. 12/380,308, May 25, 2010.

European Patent Office, Communication, Application No. 09716023.8, Oct. 8, 2010.

Applicant, Response to European Patent Office Oct. 8, 2010 Communication, Application No. 09716023.8, Nov. 17, 2010.

Bleul, et al., The Lymphocyte Chemoattractant SDF-1 is a Ligand for LESTR/fusin and Blocks HIV-1 Entry, Nature 382:829-833, 1996.

Calderon, et al., A Role for CXCL12 (SDF-1alpha) in the Pathogenesis of Multiple Sclerosis: Regulation of CXCL12 Expression in Astrocytes by Soluble Myelin Basic Protein, J. Neuroimmunol. 177:27-39, 2006.

Chong, et al., Targeting the CXCR4/CXCL12 Axis in Systemic Lupus Erythematosus, Expert Opin. Ther. Targets 13 (10):1147-1153, 2009.

Chung, et al., CXC Chemokine Receptor 4 Expressed in T Cells Plays an Important Role in the Development of Collagen-Induced Arthritis, Arthritis Res. Ther. 12:R188, 2010.

D'Souza, et al., Chemokines and HIV-1 Second Receptors—Confluence of Two Fields Generates Optimism in AIDS Research, Nat. Med. 2(12):1293-1300, 1996.

D'Souza, et al., Current Evidence and Future Directions for Targeting HIV Entry—Therapeutic and Prophylactic Strategies, JAMA 284(2):215-222, 2000.

Feng, et al., HIV-1 Entry Cofactor: Functional cDNA Cloning of a Seven-Transmembrane, G Protein-Coupled Receptor, Science 272:872-879, 1996.

Kohler, et al., Antagonism of the Chemokine Receptors CXCR3 and CXCR4 Reduces the Pathology of Experimental Autoimmune Encephalomyelitis, Brain Pathol. 18:504-516, 2008.

Krumbholz, et al., Chemokines in Multiple Sclerosis: CXCL12 and CXCL13 Up-Regulation is Differentially Linked to CNS Immune Cell Recruitment, Brain 129:200-211, 2006.

Miedema, et al., Changing Virus-Host Interactions in the Course of HIV-1 Infection, Immunol. Rev. 140:35-72, 1994.

Pistoia, V. et al. "Lymphoproliferative Disorders and Chemokines." Current Drug Targets, vol. 7 (2006): 81-90.

Wu, X. et al. "Cutaneous T-Cell Lymphoma: Roles for Chemokines and Chemokine Receptors." Journal of Investigative Dermatology, vol. 129 (2009): 1115-1119.

Drury, L. et al. "Monomeric and dimeric CXCL12 inhibit metastasis through distinct CXCR4 interactions and signaling pathways." PNAS, vol. 108, No. 43 (2011): 17655-17660.

Takekoshi, T. et al. "A locked, dimeric CXCL12 variant effectively inhibits pulmonary metastasis of CXCR4-expressing melanoma cells due to enhanced serum stability." Mol Cancer Ther (2012): 1-18.

Peled, A. et al. "Role of CXCR4 in the Pathogenesis of Acute Myeloid Leukemia." Theranostics, vol. 3, No. 1 (2013): 34-39.

\* cited by examiner

A

KPVSLSYRCPCRFFESHVARANVKHLKILNTPNCACQIVARLKNNNRQVCIDPKLKWIQEYLEKCLNK
        10        20        30        40        50        60

KPVSLSYRCPCRFFESHVARANVKHLKILNTPNCACQIVARLKNNNRQVCIDPKLKWIQEYLEKCLNK

SEQ ID NO: 1

SEQ ID NO: 2

```
         1         10        20        30      38
       gsMEGISIYTSDNYTEEMGSGDYDSMKEPAFREENANFNK
```

ENGINEERED CXCL12 ALPHA LOCKED DIMER POLYPEPTIDE

CROSS-REFERENCE TO RELATED APPLICATIONS

This application is a continuation application of U.S. Non-Provisional application Ser. No. 12/380,308, filed Feb. 26, 2009 and issued as U.S. Pat. No. 7,923,016 on Apr. 12, 2011, which claims priority to U.S. Provisional Application No. 61/067,273 filed Feb. 27, 2008, the entirety of which are hereby incorporated by reference herein for all purposes.

STATEMENT REGARDING FEDERALLY SPONSORED RESEARCH OR DEVELOPMENT

The present invention was made with United States government support awarded by the following agency: National Institute of Health-NIAID, Grant No. AI058072. The United States Government has certain rights in the invention.

FIELD OF THE INVENTION

The invention relates generally to a novel CXCL12-$\alpha_2$ locked dimer polypeptide, pharmaceutical compositions thereof, and methods of using said dimer in the treatment of cancer and autoimmune, inflammatory disease and HIV/AIDS.

BACKGROUND

Chemokines are a superfamily of chemoattractant cytokine proteins which primarily serve to regulate a variety of biological responses and promote the recruitment and migration of multiple lineages of leukocytes and lymphocytes to a body organ tissue. Chemokines are classified into four families according to the relative position of the first two cysteine residues in the protein. In one family, the first two cysteines are separated by one amino acid residue (the CXC chemokines) and in another family the first two cysteines are adjacent (the CC chemokines). In a third family, the first two cysteines are separated by three amino acids ($CX_3C$ chemokines). In a fourth family there is only one cysteine in the amino terminus (C chemokines).

The molecular targets for chemokines are cell surface receptors. One such receptor is CXC chemokine receptor 4 (CXCR4), which is a seven transmembrane G-protein coupled receptor (GPCR). CXCR4 is widely expressed on cells of hematopoietic origin, and is a major co-receptor with $CD4^+$ for certain strains of human immunodeficiency virus 1 (HIV-1).

CXCL12, formerly known as stromal cell-derived factor-1 (SDF-1), is an alpha or CXC type 7.8 kDa CXC chemokine CXCL12 is the only known natural ligand for CXCR4, as high affinity CXCL12 binding requires the CXCR4 amino terminus. CXCL12 comprises two closely related members: CXCL12-α and CXCL12-β, the native amino acid sequences of which are known, as are the genomic sequences encoding these proteins (U.S. Pat. No. 5,563,048 and U.S. Pat. No. 5,756,084, both of which are incorporated by reference herein for all purposes).

Originally described as a growth factor for bone marrow developing B cells, CXCL12 was subsequently characterized as a chemoattractant for T cells and monocytes. Genetic ablation of CXCR4 or CXCL12 results in defects in haematopoiesis, vascularization of the intestines, cerebellar formation and heart development. Similar embryonic defects in either of those chemokine receptor or chemokine gene deficient animals has revealed roles for CXCR4-CXCL12 signaling in cardiovascular, neuronal, and hematopoietic stem cell development as well as gastrointestinal vascularization. Previous studies have also established a role for CXCL12 and CXCR4 in gut vascularization, a key process in mucosal immunity and homeostasis. In vitro, CXCL12 stimulates chemotaxis of a wide range of cells including monocytes and bone marrow derived progenitor cells. Particularly notable is its ability to stimulate a high percentage of resting and activated T-lymphocytes.

Consistent with the fact that CXCR4 is a major co-receptor for HIV, CXCL12 has also been shown to block HIV entry into CD4+ cells. CXCR4 is a co-receptor for T-tropic (X4) strains of HIV, which target $CD4^+$ T cells, and CXCL12 can inhibit HIV-1 infection by preventing gp120 binding to CXCR4 and the subsequent gp41 mediated fusion. CXCR4 co-receptor usage correlates with AIDS onset, even though CCR5 is the primary co-receptor for most HIV infections.

Efforts have been made to identify CXCL12-derived peptides that interfere selectively with HIV entry, and not with CXCL12 signaling. A wide range of potential CXCR4 binding fragments of CXCL12 have been proposed for use in blocking HIV infection, indicating that the anti-HIV activity of CXCL12, or fragments of CXCL12, does not depend on antagonism of the CXCR4 receptor.

CXCL12 also directs homeostatic immune cell trafficking and inflammatory responses. Chemokine activation of specific G-protein coupled receptors (GPCR) directs cell migration toward higher chemokine concentration.

Additionally, CXCL12 and CXCR4 mediate cancer cell migration and metastasis. Treatment with CXCR4-neutralizing antibodies reduced metastatic tumor formation in a mouse model for human breast cancer. Subsequently, over twenty cancer types have been shown to express CXCR4 and metastasize to tissues that secrete CXCL12, such as bone marrow, lung, liver and lymph nodes.

CXCL12 and CXCR4 also serve to establish a niche environment for hematopoetic stem cells in bone marrow such that blocking the function of CXCL12 leads to mobilization of said stem cells so that they exit the bone marrow and enter the blood stream.

Accordingly, there is a current need for cost-effective pharmaceutical agents and treatment methods for treating various conditions including autoimmune or inflammation disorders, immune suppression conditions, infections, blood cell deficiencies, cancers and other described conditions and to mobilize stem cells by manipulating and controlling CXCL12 and CXCR4.

SUMMARY OF THE INVENTION

The inventors have engineered a novel CXCL12-$\alpha_2$ locked dimer polypeptide comprising two monomers linked together. The dimer will/might be useful in treating various conditions including cancer, autoimmune disorders and/or inflammation disorders. In one preferred embodiment the dimer comprises two monomers bound together, wherein at least one monomer has the amino acid sequence as shown in SEQ ID NO:1.

In another embodiment, the present invention provides a composition comprising a CXCL12-$\alpha_2$ locked dimer polypeptide and a pharmaceutically acceptable carrier or diluent.

In another embodiment, the present invention provides an isolated CXCL12-$\alpha_2$ locked dimer polypeptide, wherein the dimer preferably consists of at least one monomer having the amino acid sequence as shown in SEQ ID NO:1.

In another embodiment, the present invention provides a method of treating an autoimmune disease in a subject comprising administering to the subject a therapeutically effective amount of a composition comprising a CXCL12-$\alpha_2$ locked dimer.

In another embodiment, the present invention provides a method of treating a tumor in a subject comprising administering to the subject a therapeutically effective amount of a composition comprising a CXCL12-$\alpha_2$ locked dimer polypeptide.

In another embodiment, the present invention provides a method of treating HIV/AIDS in a subject comprising administering to the subject a therapeutically effective amount of a composition comprising a CXCL12-$\alpha_2$ locked dimer polypeptide.

In another embodiment, the present invention provides a method of inhibiting angiogenesis in a subject by administering to the subject a therapeutically effective amount of a composition comprising a CXCL12-$\alpha_2$ locked dimer polypeptide.

In another embodiment, the present invention provides a method of inhibiting blood cancers in a subject by administering to the subject a therapeutically effective amount of a composition comprising a CXCL12-$\alpha_2$ locked dimer polypeptide.

In another embodiment, the present invention provides a kit comprising a CXCL12-$\alpha_2$ locked dimer polypeptide wherein the dimer preferably comprises at least one monomer having the amino acid sequence as shown in SEQ ID NO:1, a pharmaceutically acceptable carrier or diluent, and instructional material.

BRIEF DESCRIPTION OF THE FIGURES

The present document contains at least one drawing executed in color. Copies of this patent or patent application publication with color drawings will be provided by the Office upon request and payment of the necessary fee.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention, which will be limited only by any later-filed nonprovisional applications.

It must be noted that as used herein and in the appended claims, the singular forms "a", "an", and "the" include plural references unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. All publications and patents specifically mentioned herein are incorporated by reference for all purposes including describing and disclosing the materials, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

CXCL12-α$_2$ Locked Dimer Polypeptide. In one embodiment, the invention provides a CXCL12-α$_2$ locked dimer polypeptide comprising at least two monomers. The monomers may be identical or may be non-identical. In one embodiment, at least one of the monomers has the amino acid sequence according to SEQ ID NO: 1. In alternate embodiments, both monomers have the amino acid sequence according to SEQ ID NO:1.

Figure 1:
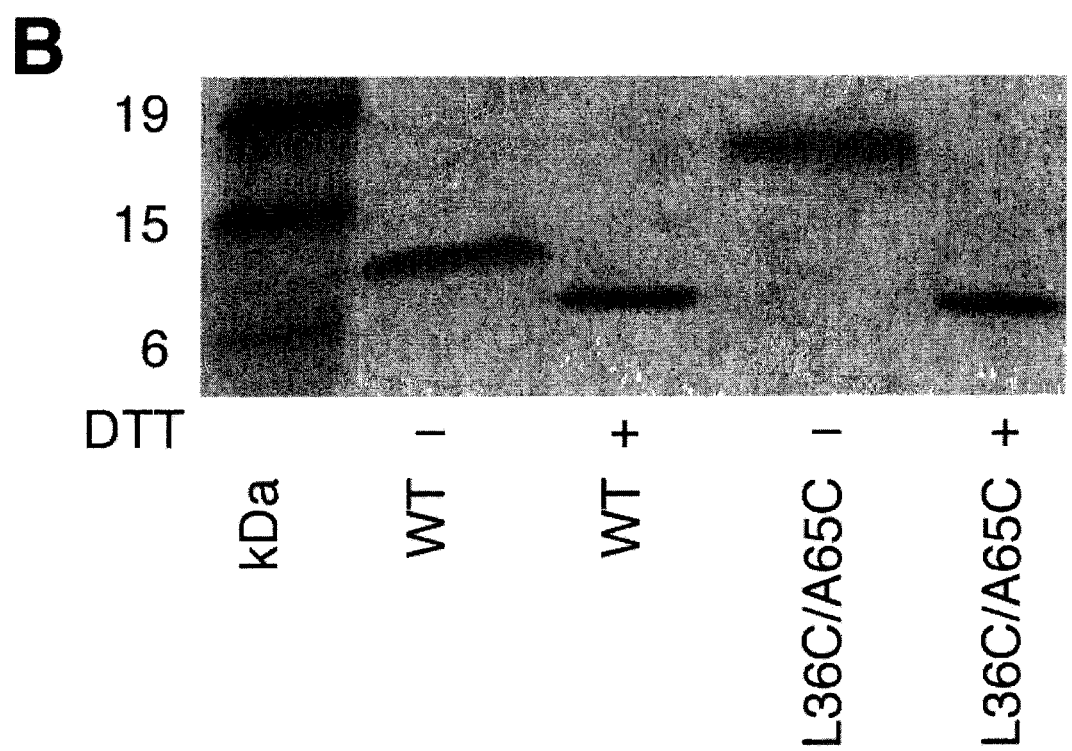
FIG. 1. CXCL12-$\alpha_2$ (L36C/A65C) (CXCL12-$\alpha_2$) is a covalently locked dimer comprising two CXCL12 L36C/A65C sequences (SEQ ID NO: 1), each sequence comprising one subunit of the dimer. The lines connecting the cysteines show where the intra- and intermolecular disulfide bonds are. A) CXCL12-$\alpha_2$ locked dimer amino acid sequence with the conserved intramolecular disulfide bonds (black lines) and the engineered intermolecular disulfide bonds (red lines) illustrated. B) SDS-PAGE of CXCL12-$\alpha$ and CXCL12-$\alpha_2$ treated with and without dithiothreitol (DTT). CXCL12-$\alpha$ and CXCL12-$\alpha_2$ migrate near the monomeric molecular weight of 8 kDa when treated with DTT. In contrast, CXCL12-$\alpha_2$ migrates as a dimer while CXCL12-$\alpha$ migrates as a monomer in the absence of DTT. C) Translational diffusion measurements of CXCL12-$\alpha_2$ indicate CXCL12-$\alpha_2$ is dimeric. Diffusion coefficients ($D_s$) of wild-type CXCL12 (black circles) in 20 mM sodium phosphate at pH 7.4 plotted versus chemokine concentration. Non-linear fitting of the CXCL12-$\alpha$ $D_s$ values indicates a dimer dissociation $K_d$ of 120 µM with a pure monomer $D_s$ value of ~1.6 ($\times 10^{-6}$ cm$^2$s$^{-1}$) and a dimer value of ~1.0 ($\times 10^{-6}$ cm$^2$s$^{-1}$). $D_s$ values for 10, 50, and 150 µM SDF1$_2$ (red triangles) range from 1.08-1.09 ($\times 10^{-6}$ cm$^2$s$^{-1}$) consistent with those expected for CXCL12-$\alpha$ in the dimeric state. D) N-terminal peptides corresponding to the first thirty-eight amino acids of CXCR4 are illustrated. The sequence for p38 is identical to that of CXCR4 except for an additional N-terminal gly-ser dipeptide (cloning artifact) and the C28A substitution (green) introduced to prevent oxidative peptide dimer formation. The sulfated peptides are identical to p38 except for the inclusion of sulfotyrosine at position 21 for p38-sY$_1$ and at positions 7, 12 and 21 for p38-sY$_3$.
Figure 1:
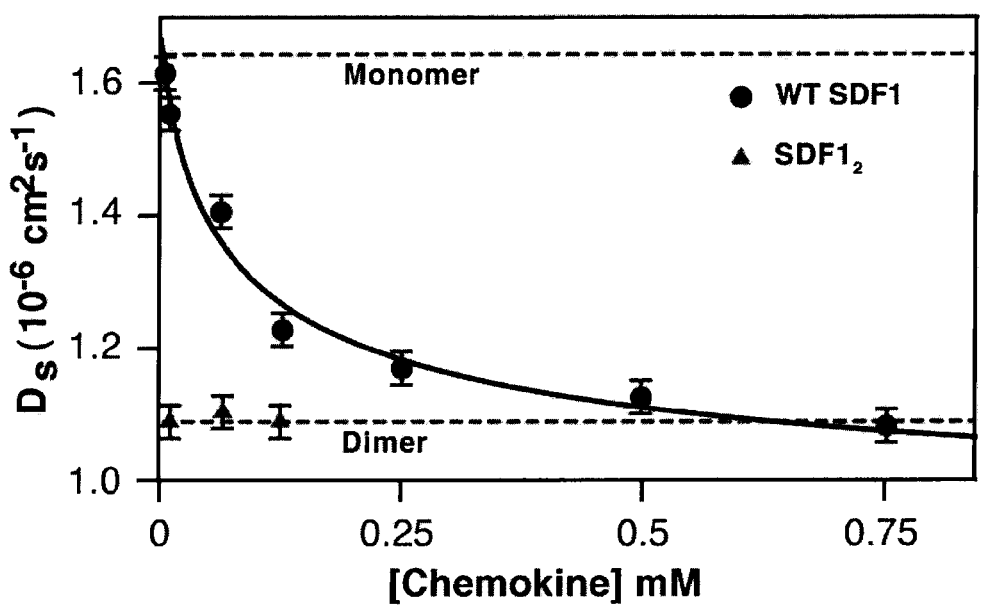
Figure 1:
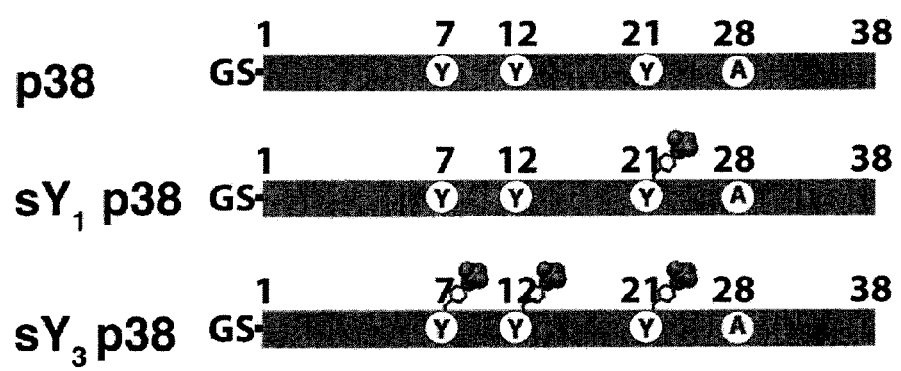

By "locked" we mean the monomer components of the polypeptide are linked to each other via at least one covalent bond. The monomer and dimer forms do not interconvert. In a preferred embodiment, at least one of residues L36 and A65 are replaced with cysteine residues to create at least one intermolecular disulfide bond between cysteine residues at position 36 of one subunit and/or position 65 of the other monomer subunit. As shown in FIG. 1A, either or both cysteine residues at positions L36 and A65 can be replaced with cysteines to form the locked dimer with at least one, but preferably two, disulfide bonds.

Other residue(s) besides L36C and A65C in CXCL12 could be mutated to cysteines in order to form the locked dimer similar to the one of the present invention. For instance, a locked dimer can be created by mutating amino acid(s) in the CXCL12 dimer interface to cysteines that are positioned opposite one another yielding a disulfide bond that covalently links two CXCL12 monomers. For example, residue K27 is directly across the CXCL12 dimer interface from residue K27 of the opposing subunit and K27C mutation would likely make a locked dimer. Residues L26 and I28 are also on the CXCL12 dimer interface, and a L26C/I28C variant should form a locked dimer with L26C of one monomer subunit forming a disulfide bond with I28C of the opposing subunit and I28C of one monomer subunit forming a disulfide bond with L26C of the opposing subunit.

In a preferred embodiment, the CXCL12α$_2$ locked dimer of the present invention has substitutions at both L36C/A65C residues. Residue L36 is on beta strand 2 and A65 is near the end of the alpha helix of the dimer. Thus, disulfide bonds form between beta strand 2 and the end of the helix generate the locked dimer. A similar locked dimer could be created using disulfide bonds introduced between beta strand 1 and the middle of the alpha helix. For example, CXCL12 with I28C/Y61C or I28C/L62C would form a locked dimer with beta strand one of one monomer having a disulfide bond to the middle of the alpha helix of the second monomer thus making a locked dimer. Additionally, a locked dimer may be created by generating a construct that produces two CXCL12 monomers where the C-terminus of one is linked to the N-terminus of the other through an amino acid linker.

Additional methods for making locked dimers of CXCL12 could also include other types of covalent linkages besides disulfide bonds including, but not limited to, chemical cross-linking reagents.

In a preferred embodiment, the locked dimer of the present invention comprises a substantially pure preparation. By "substantially pure" we mean a preparation in which more than 90%, e.g., 95%, 98% or 99% of the preparation is that of the locked dimer.

In a preferred embodiment, at least one of the monomers comprising the locked dimer of the present invention has the amino acid sequence as shown in SEQ ID NO:1 or a homologue or fragment thereof. In a further preferred embodiment, the dimer comprises two monomers having the amino acid sequence as shown in SEQ ID NO:1 or a homologue or variant thereof. By "homologue" we mean an amino acid sequence generally being at least 80%, preferably at least 90% and more preferably at least 95% homologous to the polypeptide of SEQ ID NO:1 over a region of at least twenty contiguous amino acids. By "fragment," we mean peptides, oligopeptides, polypeptides, proteins and enzymes that comprise a stretch of contiguous amino acid residues, and exhibit substantially a similar, but not necessarily identical, functional activity as the complete sequence. Fragments of SEQ ID NO:1, or their homologues, will generally be at least ten, preferably at least fifteen, amino acids in length, and are also encompassed by the term "a CXCL12 monomer" as used herein.

Mutations known to prevent degradation of CXCL12 or increase the in vivo half life may also be incorporated into the CXCL12α$_2$ sequence. For instance, adding a serine to the N-terminus along with a S4V substitution prevent CXCL12 degradation by proteases. Therefore, adding a serine to the N-terminus would likely similarly prevent protease degradation of the CXCL12α$_2$ locked dimer of the present invention.

Further, in addition to binding CXCR4, CXCL12 also binds to heparin found in the extracellular matrix on cell surfaces. The inventors have shown that the CXCL12α$_2$ locked dimer of the present invention also binds heparin. Amino acid substitutions in CXCL12, including K24S, K27S, or K24S/K27S can prevent heparin binding and increase the half-life of CXCL12 in vivo; therefore, similar mutations in CXCL12α$_2$ would likely prevent heparin binding and increase the in vivo half-life of the dimer.

CXCL12α$_2$ variants have been generated that have a gly-met dipeptide on the N-terminus. N-terminal extensions to CXCL12 prevent CXCR4 activation and thus inclusion in CXCL12α$_2$ may increase its effectiveness. Additionally, it may be useful to create CXCL12α$_2$ variants where both subunits are not identical. For example, only one monomer of the CXCL12α$_2$ dimer may need to include the addition of an N-terminal serine and a S4V substitution or the lysine substitutions for the prevention of heparin binding. Alternatively, a CXCL12α$_2$ variant where the N-terminus of one monomer has the native sequence but the other has been extended may have different or enhanced pharmacological properties compared to CXCL12α$_2$.

The locked CXCL12 dimer could also be incorporated into a larger protein or attached to a fusion protein that may function to increase the half life of the dimer in vivo or be used as a mechanism for time released and/or local delivery (U.S. Patent Appn. No. 20060088510).

In another embodiment, the invention provides an isolated CXCL12-$\alpha_2$ locked dimer polypeptide as described above. By "isolated" we mean a nucleic acid sequence that is identified and separated from at least one component or contaminant with which it is ordinarily associated. An isolated nucleic acid is present in a form or setting that is different from that in which it is found in nature. In contrast, non-isolated nucleic acids such as DNA and RNA are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, an isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

CXCL12-$\alpha_2$ locked dimer polypeptides of the present invention can be prepared by standard techniques known in the art. The peptide component of CXCL12-$\alpha_2$ is composed, at least in part, of a peptide, which can be synthesized using standard techniques such as those described in Bodansky, M. Principles of Peptide Synthesis, Springer Verlag, Berlin (1993) and Grant, G. A. (ed.). Synthetic Peptides: A User's Guide, W.H. Freeman and Company, New York (1992). Automated peptide synthesizers are commercially available (e.g., Advanced ChemTech Model 396; Milligen/Biosearch 9600). Additionally, one or more modulating groups can be attached to the CXCL12-$\alpha_2$ derived peptidic component by standard methods, such as by using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)). Exemplary syntheses of preferred CXCL12-$\alpha_2$ locked dimer polypeptides according to the present invention are described further in the Examples below.

Peptides of the invention may be chemically synthesized using standard techniques such as those described in Bodansky, M. Principles of Peptide Synthesis, Springer Verlag, Berlin (1993) and Grant, G. A. (ed.). Synthetic Peptides: A User's Guide, W.H. Freeman and Company, New York, (1992) (all of which are incorporated herein by reference).

In another aspect of the invention, peptides may be prepared according to standard recombinant DNA techniques using a nucleic acid molecule encoding the peptide. A nucleotide sequence encoding the peptide can be determined using the genetic code and an oligonucleotide molecule having this nucleotide sequence can be synthesized by standard DNA synthesis methods (e.g., using an automated DNA synthesizer). Alternatively, a DNA molecule encoding a peptide compound can be derived from the natural precursor protein gene or cDNA (e.g., using the polymerase chain reaction (PCR) and/or restriction enzyme digestion) according to standard molecular biology techniques.

CXCL12-$\alpha_2$ Locked Dimer Polypeptide Pharmaceutical Compositions. In another embodiment, the invention provides a composition comprising a substantially pure CXCL12-$\alpha_2$ locked dimer polypeptide of the present invention, and a pharmaceutically acceptable carrier. By "pharmaceutically acceptable carrier" we mean any and all solvents, dispersion media, coatings, antibacterial and antifungal agents, isotonic and absorption delaying agents, and the like that are physiologically compatible. In one embodiment, the carrier may be suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, membrane nanoparticle or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, such as, monostearate salts and gelatin.

Moreover, the CXCL12-$\alpha_2$ locked dimer polypeptide of the present invention can be administered in a time-release formulation, such as in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. CXCR4 antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The CXCL12-$\alpha_2$ locked dimer polypeptide of the present invention also may be formulated with one or more additional compounds that enhance the solubility of the CXCL12-$\alpha_2$ locked dimer polypeptide.

Administration. The CXCL12-$\alpha_2$ locked dimer polypeptide of the present invention, optionally comprising other pharmaceutically active compounds, can be administered to a patient orally, rectally, parenterally, (e.g., intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the CXCL12-$\alpha_2$ locked dimer of the invention combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (e.g., propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the CXCL12-$\alpha_2$ locked dimer polypeptide is provided in dry (i.e., powder or granular) form for reconstitution with a suitable vehicle (e.g., sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The CXCL12-$\alpha_2$ locked dimer polypeptide of the present invention may also contain adjuvants such as suspending, preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, such as aluminum monostearate and/or gelatin.

Dosage forms can include solid or injectable implants or depots. In preferred embodiments, the implant comprises an effective amount of the $\alpha_2$ locked dimer polypeptide and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly($\epsilon$-caprolactone), a polyanhydride, a poly(beta-hydroxy butyrate), a poly(ortho ester) and a polyphosphazene. In other embodiments, the implant comprises an effective amount of CXCL12-$\alpha_2$ locked dimer polypeptide and a silastic polymer. The implant provides the release of an effective amount of CXCL12-$\alpha_2$ locked dimer polypeptide for an extended period ranging from about one week to several years.

Solid dosage forms for oral administration include capsules, tablets, powders, and granules. In such solid dosage forms, the CXCL12-$\alpha_2$ locked dimer polypeptide is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Tablets may be manufactured with pharmaceutically acceptable excipients such as inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Dose Requirements. In particular embodiments, a preferred range for therapeutically or prophylactically effective amounts of CXCL12-$\alpha_2$ locked dimer polypeptide may be 0.1 nM-0.1M, particularly 0.1 nM-0.05M, more particularly 0.05 nM-15 µM and most particularly 0.01 nM-10 µM. It is to be noted that dosage values may vary with the severity of the condition to be alleviated, especially with multiple sclerosis. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of CXCL12-$\alpha_2$ locked dimer polypeptide in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such as active compound for the treatment of sensitivity in individuals.

Methods of Use. The invention also provides corresponding methods of use, including methods of medical treatment, in which a therapeutically effective dose of a CXCL12-$\alpha_2$ locked dimer polypeptide, preferably wherein the dimer comprises at least one monomer having the amino acid sequence according to SEQ ID NO:1, is administered in a pharmacologically acceptable formulation. Accordingly, the invention also provides therapeutic compositions comprising a CXCL12-$\alpha_2$ locked dimer polypeptide and a pharmacologically acceptable excipient or carrier, as described above. The therapeutic composition may advantageously be soluble in an aqueous solution at a physiologically acceptable pH.

In one embodiment, the invention provides a method of treating autoimmune disease in a subject comprising administering to the subject a therapeutically effective amount of a composition comprising a CXCL12-$\alpha_2$ locked dimer polypeptide. By "autoimmune disease" we mean illnesses generally understood to be caused by the over-production of cytokines, lymphotoxins and antibodies by white blood cells, including in particular T-cells. Such autoimmune diseases include but are not limited to Multiple Sclerosis (MS), Guillain-Barre Syndrome, Amyotrophic Lateral Sclerosis, Parkinson's disease, Alzheimer's disease, Diabetes Type I, gout, lupus, and any other human illness that T-cells play a major role in, such as tissue graft rejection. In addition, diseases involving the degradation of extra-cellular matrix include, but are not limited to, psoriatic arthritis, juvenile arthritis, early arthritis, reactive arthritis, osteoarthritis, ankylosing spondylitis. osteoporosis, muscular skeletal diseases like tendonitis and periodontal disease, cancer metastasis, airway diseases (COPD, asthma or other reactive airways disease), renal and liver fibrosis, cardio-vascular diseases like atherosclerosis and heart failure, and neurological diseases like neuroinflammation and multiple sclerosis. Diseases involving primarily joint degeneration include, but are not limited to, rheumatoid arthritis, psoriatic arthritis, juvenile arthritis, early arthritis, reactive arthritis, osteoarthritis, ankylosing spondylitis. Diseases involving the eye include, but are not limited to autoimmune uveitis and uveoconjunctivitis and dry eye syndrome. Diseases involving post-infections complications of viral or bacterial diseases such as glomerulonephritis, vasculitis, meningoencephalitis. Diseases involving the gastrointestinal system include but are not limited to inflammatory bowel diseases.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex.

By "treating" we mean the management and care of a subject for the purpose of combating the disease, condition, or disorder. The terms embrace both preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the locked dimer of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the locked dimer of the present invention is administered to a subject or is used in an assay or other method described herein or a cited reference, e.g., within about 1 hour of the administration or use of the locked dimer of the present invention to about 3, 6, 9 months or more after a subject(s) has received the locked dimer of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the locked dimer of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the locked dimer of the present invention is administered to a subject or is used in an assay or other method described herein or a cited reference, e.g., within about 1 hour of the administration or use of the locked dimer of the present invention to about 3, 6, 9 months or more after a subject(s) has received the locked dimer of the present invention.

By "administering" we mean any means for introducing the CXCL12-$\alpha_2$ locked dimer polypeptide of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

By "therapeutically effective amount" we mean an amount effective, at dosages and for periods of time necessary, to achieve the desired therapeutic result, such as reduction or reversal of angiogenesis in the case of cancers, or reduction or inhibition of T-cells in autoimmune diseases. A therapeutically effective amount of the CXCL12-$\alpha_2$ locked dimer polypeptide may vary according to factors such as the disease state, age, sex, and weight of the subject, and the ability of the CXCL12-$\alpha_2$ locked dimer polypeptide to elicit a desired response in the subject. Dosage regimens may be adjusted to provide the optimum therapeutic response. A therapeutically effective amount is also one in which any toxic or detrimental effects of the CXCL12-$\alpha_2$ locked dimer polypeptide are outweighed by the therapeutically beneficial effects.

A "prophylactically effective amount" refers to an amount effective, at dosages and for periods of time necessary, to achieve the desired prophylactic result, such as preventing or inhibiting the rate of metastasis of a tumor or the onset of bouts or episodes of multiple sclerosis. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In another embodiment, the invention provides a method of treating a tumor in a subject comprising administering to the subject a therapeutically effective amount of a composition comprising a CXCL12-$\alpha_2$ locked dimer polypeptide. By "tumor" we mean any abnormal proliferation of tissues, including solid and non-solid tumors. For instance, the composition and methods of the present invention can be utilized to treat cancers that manifest solid tumors such as breast cancer, colon cancer, lung cancer, thyroid cancer, ovarian cancer and the like. The composition and methods of the present invention can also be utilized to treat non-solid tumor cancers such as non-Hodgkin's lymphoma, leukemia and the like.

In another embodiment, the present invention provides a method of inhibiting angiogenesis in a subject by administering to the subject a therapeutically effective amount of a composition comprising a CXCL12-$\alpha_2$ locked dimer polypeptide. By "angiogenesis" we mean the process whereby new blood vessels penetrate tissue thus supplying oxygen and nutrients while removing waste in various pathological conditions including but not limited to diabetic retinopathy, macular degeneration, rheumatoid arthritis, inflammatory bowel disease, cancer, psoriasis, osteoarthritis, ulcerative colitis, Crohn's disease and coronary thrombosis.

In another embodiment, the present invention provides a method of treating inflammation in a subject by administering to the subject a therapeutically effective amount of a composition comprising a CXCL12-$\alpha_2$ locked dimer polypeptide. By "inflammation" we mean the complex biological response of vascular tissues to harmful stimuli, such as pathogens, damaged cells, or irritants. It is a protective attempt by the organism to remove the injurious stimuli as well as initiate the healing process for the tissue. For instance, the composition and methods of the present invention can be utilized to treat inflammation associated with: an allergic disease such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy; a neurodegenerative disease; a cardiovascular disease; a gastrointestinal disease; a tumor such as a malignant tumor, a benign tumor, a solid tumor, a metastatic tumor and a non-solid tumor; septic shock; anaphylactic shock; toxic shock syndrome; cachexia; necrosis; gangrene; a prosthetic implant such as a breast implant, a silicone implant, a dental implant, a penile implant, a cardiac implant, an artificial joint, a bone fracture repair device, a bone replacement implant, a drug delivery implant, a catheter, a pacemaker and a respirator tube; menstruation; an ulcer such as a skin ulcer, a bed sore, a gastric ulcer, a peptic ulcer, a buccal ulcer, a nasopharyngeal ulcer, an esophageal ulcer, a duodenal ulcer and a gastrointestinal ulcer; an injury such as an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound; a musculo-skeletal inflammation such as a muscle inflammation, myositis, a tendon inflammation, tendinitis, a ligament inflammation, a cartilage inflammation, a joint inflammation, a synovial inflammation, carpal tunnel syndrome and a bone inflammation.

In another embodiment, the locked dimer of the present invention may also provide for the down regulation of cell surface expression of CXCR4 without activating the chemotaxis machinery of said cells. In another embodiment, the locked dimer of the present invention may enhance the efficacy of CXCR4 receptor pharmacological antagonists or HIV-1 entry blockers by decreasing the cell surface expression of CXCR4.

Kits. In another embodiment, the present invention provides a kit comprising a pharmaceutical composition according to the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention may also further comprise a delivery device for delivering the composition to a subject. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

The delivery device may comprise a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

III. Examples

The following examples describing materials and methodology are offered for illustrative purposes only, and are not intended to limit the scope of the present invention.

Detection of 2:1 p38: CXCL12-$\alpha_2$ locked dimer polypeptide binding. Binding the wild-type CXCL12-$\alpha$ with p38 requires navigating a complex set of coupled binding equilibria to permit exchange between complexes with stoichiometries of 1:1, 1:2, 2:1 and 2:2. Because only one set of CXCL12-$\alpha_2$ locked dimer signals is observed during the p38 titration and addition of more than two molar equivalents of p38 induces no further chemical shift perturbations, the inventors concluded that a symmetric 2:1 p38: CXCL12-$\alpha_2$ locked dimer complex is formed (see Example 3).

Figure 4:
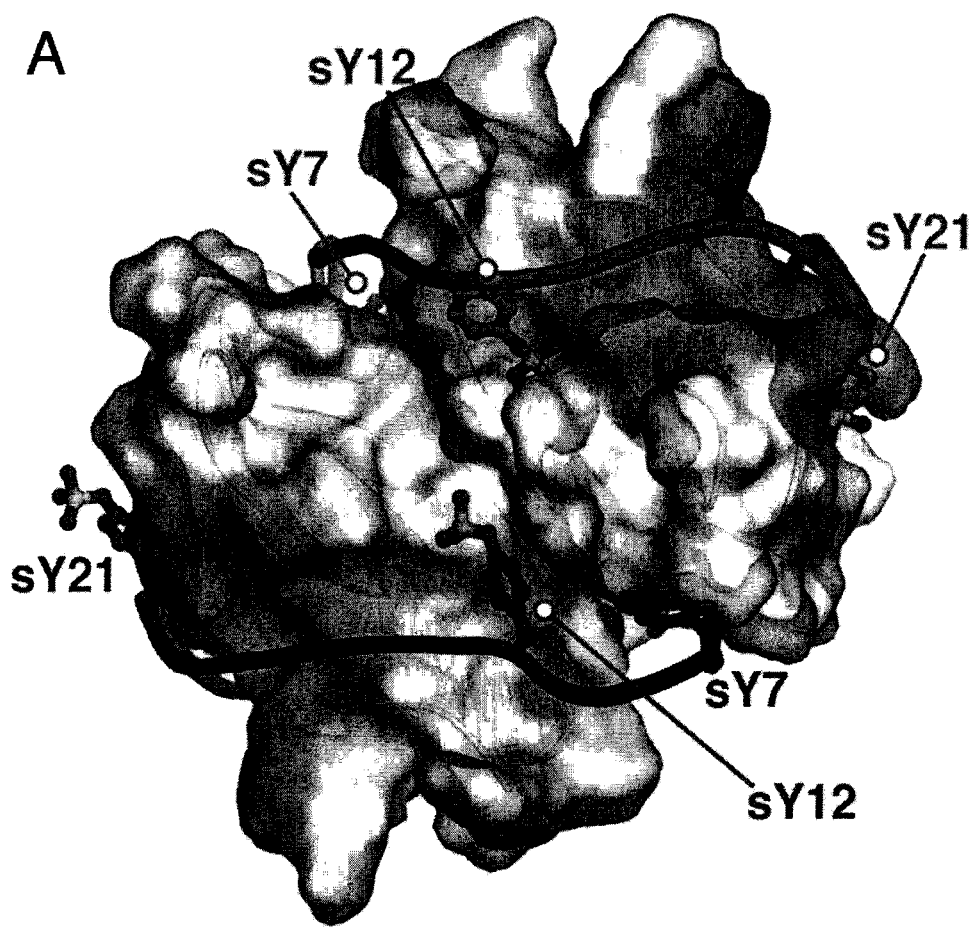
FIG. 4. Recognition of sulfotyrosine by CXCL12-$\alpha_2$. A) NMR structure of CXCL12-$\alpha_2$ bound to p38-sY$_3$. Individual monomers of the symmetric CXCL12-$\alpha_2$ dimer are shown in tan and white with symmetry-related p38-sY$_3$ peptides in blue and orange. Chemical shift perturbations greater than 0.25 ppm (FIG. 1C) are highlighted in green on the surface of the CXCL12-$\alpha_2$ surface. Flexible regions of CXCL12-$\alpha_2$ (residues 1-8) and p38-sY$_3$ (residues 29-38) are omitted for clarity. Sulfotyrosine side chains are shown in ball-and-stick representation. In panels B-D, basic residues in CXCL12-$\alpha_2$ that pair with CXCR4 sulfotyrosines are shown in blue and CXCL12-$\alpha_2$ residues with NOEs to the sulfotyrosines are shown in green. B) CXCR4 sY7 binds CXCL12-$\alpha_2$ near R20 and makes NOE contacts with V23. C) CXCR4 sY12 occupies a cleft bounded by CXCL12-$\alpha_2$ residues K27, P10 and L29. D) CXCR4 sY21 pairs with CXCL12-$\alpha_2$ R47 and makes NOE contacts with V18 and V49.
Figure 4:
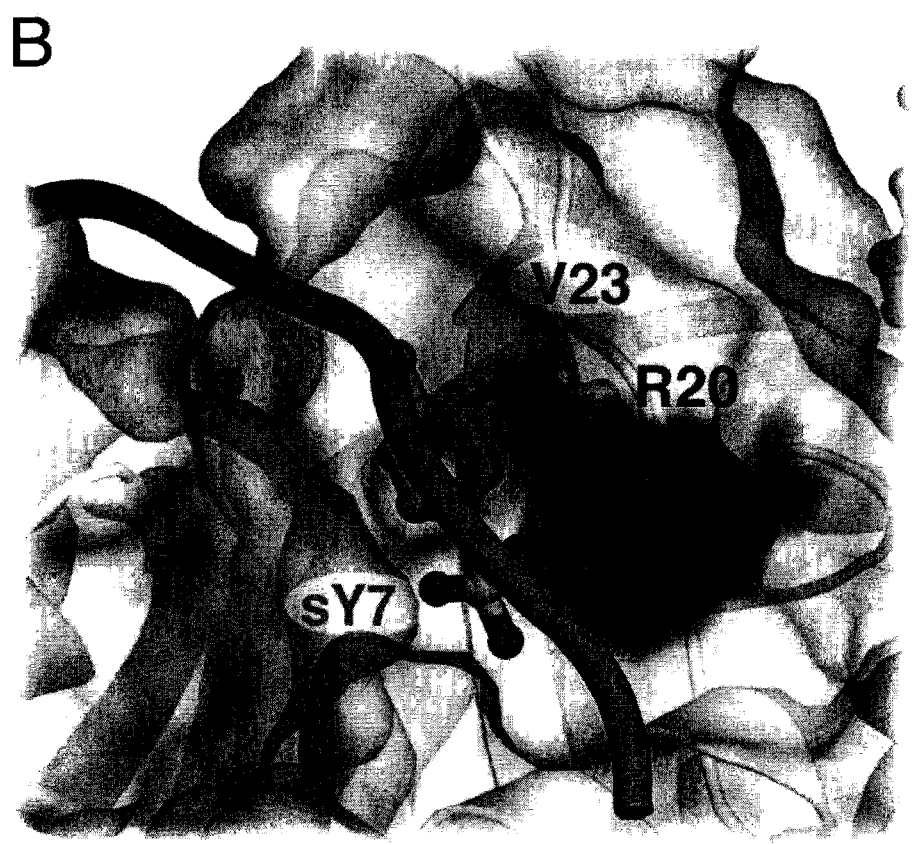
Figure 4:
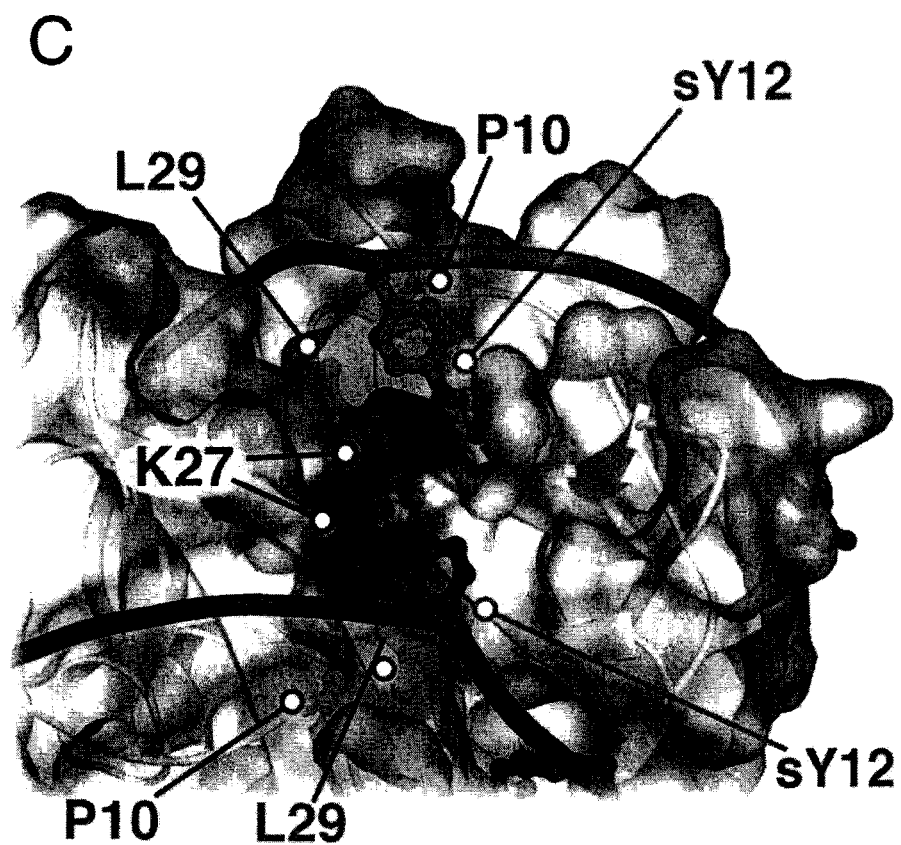
Figure 4:
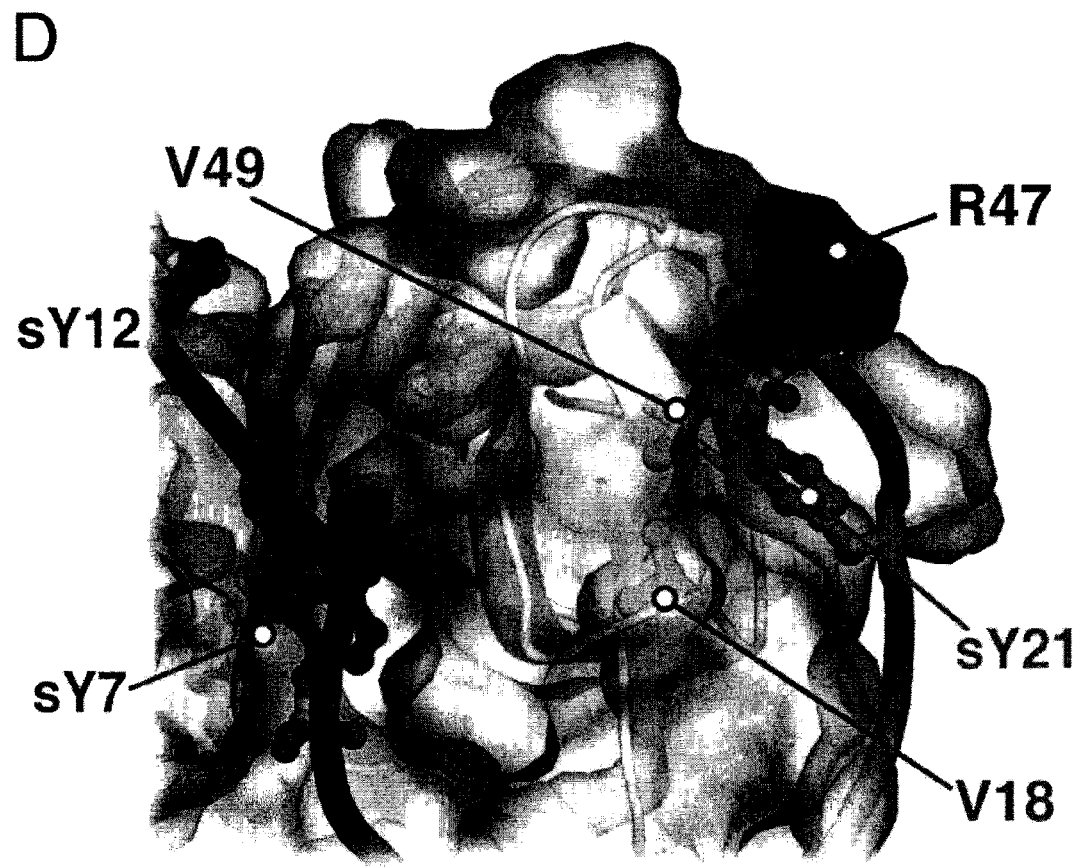

Structure analysis of CXCL12-$\alpha_2$ locked dimer polypeptide individual sulfotyrosine recognition sites. Structures of sulfotyrosine-containing protein complexes show that the sulfonate group typically interact with a positively charged side chain. Each negatively-charged sulfotyrosine side chains docks into a unique positively-charged pocket on the CXCL12-$\alpha_2$ surface (FIG. 4), and the inventors designed a series of amino acid substitutions in wild-type CXCL12-$\alpha$ to individually disrupt those binding sites (see Example 4 and Table 5).

Structure of CXCL12-$\alpha_2$ locked dimer polypeptide bound to sulfated p38 peptides. CXCR4 stabilizes the CXCL12-$\alpha_2$ dimer by interacting with both subunits and recognizing unique features of the CXCL12-$\alpha_2$ dimer interface. Near the CXCR4 N-terminus, each p38 peptide crosses the CXCL12-$\alpha_2$ dimer interface, such that sY7 and sY12 interact with opposing CXCL12-$\alpha$ monomers. In the membrane-proximal portion of the CXCR4 N-terminal domain, P27 inserts between Q59 of one CXCL12-$\alpha_2$ subunit and L66 of the opposing subunit, where the C-terminal helices from each monomer pack against each other (see Example 5).

Inhibitory Effect of the CXCL12-$\alpha_2$ locked dimer polypeptide on cell migration. The inventors data shows that the CXCL12-$\alpha_2$ locked dimer inhibits chemotaxis induced by wild-type CXCL12-$\alpha$. The CXCL12-$\alpha_2$ locked dimer inhibits chemotaxis induced by wild-type CXCL12-$\alpha$ with an IC$_{50}$ of approximately 4 nM (FIG. 5D). The inventors' results show that monomer CXCL12-$\alpha$ activates cell migration while the dimeric CXCL12-$\alpha_2$ halts cell migration. The results also demonstrate that the CXCL12-$\alpha_2$ locked dimer acts as a partial CXCR4 agonist (as evidenced by the detection of the secondary messenger calcium) and as a selective antagonist that blocks chemotaxis. This indicates that the CXCL12-$\alpha_2$ locked dimer is a tool for correlating cellular responses with different intracellular signaling pathways initiated by CXCR4. Also, the CXCL12-$\alpha_2$ locked dimer of the present invention may be useful in the development of anti-metastatic agents by preventing CXCL12-$\alpha$/CXCR4-mediated migration of circulating cancer cells (see Example 6).

Physiological relevance of the CXCL12-$\alpha 2$ locked dimer. Despite being obtained with a constitutively dimeric chemokine, CXCL12-$\alpha_2$:p38 structures correctly identify key elements of CXCR4 recognition by wild-type CXCL12-$\alpha$. The inventors monitored activation of CXCR4 using THP-1 cells and a similar Ca$^{2+}$-flux assay. Robust CXCR4 activation was observed with both wild-type CXCL12-$\alpha$ (EC$_{50}$=3.6 nM) and CXCL12-$\alpha_2$ (EC$_{50}$=12.9 nM) (FIG. 5A). AMD3100, a small-molecule CXCR4 antagonist, inhibited both proteins with IC$_{50}$ values of 3.3 nM (CXCL12-A) and 3.2 nM (CXCL12-$\alpha_2$), demonstrating that the observed calcium flux responses were mediated by CXCR4. Thus, the inventors data shows that CXCL12-$\alpha_2$ binds and activates its cognate receptor (see Example 7).

Chemotaxis of the CXCL12-$\alpha_2$ locked dimer. Results from Ca$^{2+}$-flux assays collectively suggest that CC and CXC chemokine dimers behave differently. For instance, CC chemokines form dimers that cannot activate their cognate GPCRs, while CXC chemokine dimers are functionally indistinguishable from their monomeric counterparts. In contrast to wild-type CXCL12-$\alpha$, the constitutively dimeric CXCL12-$\alpha_2$ of the present invention failed to attract cells in a transwell chemotaxis assay even at concentrations up to 1 μM (FIG. 5B). Accordingly, the inventors results demonstrate that at low chemokine concentrations monomeric CXCL12-$\alpha$ stimulates chemotaxis, while at higher concentrations dimeric CXCL12-$\alpha_2$ halts cell migration corresponding to the second, downward half of the bell-shaped curve (see Example 8).

The activation of CXCR4 in the calcium flux assay by CXCL12-$\alpha_2$ and the inhibition of chemotaxis brings up the question of CXCL12-$\alpha_2$ CXCR4 stoichiometry. CXCR4 has been purified as a homodimer, the CXCR4 N-terminus promotes CXCL12-$\alpha$ dimer formation and the inventors' structures show two CXCR4 N-termini bound to CXCL12-$\alpha_2$. Nevertheless, the role of homo- and heterodimers in GPCR signaling remains controversial. Some place a high significance on the role of dimer formation in signaling, while others discount evidence of dimerization as an experimental artifact.

Inspection of the high resolution, dimeric crystal structure of $\beta_2$AR, a type A GPCR like CXCR4 suggests that formation of a 2:2 CXCL12-$\alpha$:CXCR4 complex is plausible. The ligand binding sites of $\beta_2$ adrenergic receptor monomers are separated by approximately 42 Å, which is the distance between the N-termini in a CXCL12-$\alpha_2$ dimer. The N-terminus of CXCL12-$\alpha$ activates the CXCR4 receptor and thus is the region of CXCL12-$\alpha$ that corresponds to small molecule agonists of GPCRs like $\beta_2$AR.

Additionally, it is reasonable to propose that wild-type CXCL12 concentrations near the IC$_{50}$ for chemotaxis prevention are physiologically plausible. Here the inventors show that the locked CXCL12-$\alpha_2$ dimer of the present invention can inhibit chemotaxis with an IC$_{50}$ of 4 nM. In the presence of the CXCR4 N-terminus the CXCL12-$\alpha$ dimer dissociation K$_d$ is 49 μM, which equates to a 4 nM dimer CXCL12-$\alpha_2$ concentration at a total CXCL12-$\alpha$ concentration of 300-400 nM. If interactions with the full-length receptor or glycosaminoglycans further enhance CXCL12-$\alpha$ self-association to yield a K$_d$ of 1 μM, CXCL12-$\alpha_2$ dimer concentrations will approach 4 nM when total CXCL12-$\alpha$ is 50 nM, a concentration within the physiological range.

The structure of CXCL12-$\alpha$ with CXCR4 provides important knowledge on the role of sulfotyrosine recognition by chemokines. The inventors' results also continue to highlight the need to address the role of chemokine oligomers in chemotaxis and show the importance of investigating each chemokine on an individual basis, since the CXCL12-$\alpha_2$ dimer can bind its receptor while MIP-1$\beta$ dimer cannot.

Additionally, both wild-type, preferentially monomeric CXCL12-$\alpha$ H25R and dimeric CXCL12-$\alpha_2$ activate CXCR4, generating the secondary messenger calcium. However, only wild-type CXCL12-$\alpha$ and CXCL12-$\alpha$ H25R can produce chemotaxis. This suggests the oligomeric state of CXCL12-$\alpha$ controls certain intracellular signals that either lead to or prevent chemotaxis. Identification of the specific signaling pathways affected by dimeric CXCL12-$\alpha_2$ will improve understanding of cell migration and may suggest intracellular targets for the prevention of cancer metastasis.

The dimeric CXCL12 blocks the normal agonistic activity of CXCL12 but does not necessarily prevent the internalization or so-called down-regulation of the target CXCR4 receptor. Hence, CXCL12$\alpha_2$ locked dimer not only blocks the chemotactic effect of CXCL12 but also the effective concentration of the CXCR4 receptor on the cell surface decreases. Thus, CXCL12$\alpha_2$ locked dimer should be expected to display a high degree of efficacy, even when compared to standard CXCR4 antagonists, which may block agonist activity, but fail to decrease receptor number.

EXAMPLE 1

Materials, Methods and Instrumentation

The production of sY$_1$ p38 has been explained and Y$_3$ p38 was generated in a similar manner. Samples for structure elucidation consisted of U-[$^{15}$N,$^{13}$C] CXCL12-$\alpha_2$ with unlabeled peptide and U-[$^{15}$N,$^{13}$C] peptide with unlabeled CXCL12-$\alpha_2$ at a 1:1.25 molar ratio of labeled to unlabeled monomers. Standard NMR techniques were use for generating chemical shift assignments for $^{15}$N/$^{13}$C labeled CXCL12-$\alpha_2$, p38, sY$_1$ p38 and sY$_1$ p38. 3D $^{15}$N-edited NOESY-HSQC, $^{13}$C-edited NOESY-HSQC, and $^{13}$C(aromatic)-edited NOESY-HSQC spectra ($\tau_{mix}$=80 ms) were used to generate distance constraints. A 3D F1-$^{13}$C-filtered/F3-$^{13}$C-edited NOESY-HSQC spectrum ($\tau_{mix}$=120 ms) was used for obtaining intermolecular distance constraints.

TALOS and the secondary shifts of the $^1$H$^\alpha$, $^{13}$C$^\alpha$, $^{13}$C$^\beta$, $^{13}$C', and $^{15}$N nuclei generated backbone phi and psi dihedral angle constraints. The NOEASSIGN module of the torsion angle dynamics program CYANA with intermolecular constraints defined was used to calculate the initial structures in an automated manner. Iterative manual refinement followed to eliminate constraint violations generating twenty conformers with the lowest target function. X-PLOR was used for further refinement, in which physical force field terms and explicit water solvent molecules were added to the experimental constraints. Tables 1-4 list the statistics for Procheck-NMR validation of the final twenty conformers.

TABLE 1

Statistics for the 20 CXCL12-$\alpha_2$ L36C A65C conformers

| Experimental constraints | |
|---|---|
| Distance constraints | |
| Long | |
| Intra- CXCL12-$\alpha$ monomer | 857 |
| Inter- CXCL12-$\alpha$ monomers | 113 |
| Medium [1 < (i − j) ≦ 5] | 300 |
| Sequential [(i − j) = 1] | 312 |
| Intraresidue [i = j] | 692 |
| Total | 2274 |
| Dihedral angle constraints ($\phi$ and $\psi$) | 138 |
| Average atomic R.M.S.D. to the mean structure (Å) | |
| Residues | |
| Backbone (C$^\alpha$, C', N) | 0.51 ± 0.05 |
| Heavy atoms | 1.05 ± 0.12 |
| Deviations from idealized covalent geometry [a] | |
| Bond lengths RMSD (Å) | 0.017 |
| Torsion angle violations RMSD (°) | 1.4 |
| WHATCHECK quality indicators | |
| Z-score | −1.52 ± 0.23 |
| RMS Z-score | |
| Bond lengths | 0.78 ± 0.02 |
| Bond angles | 0.76 ± 0.02 |
| Bumps | 0 ± 0 |
| Lennard-Jones energy [b] (kJ mol$^{-1}$) | −2927.8 ± 108.0 |
| Constraint violations [c, d] | |
| NOE distance Number > 0.5 Å | 0 ± 0 |
| NOE distance RMSD (Å) | 0.0251 ± 0.0013 |
| Torsion angle violations Number > 5° | 0.05 ± 0.22 |
| Torsion angle violations RMSD (°) | 0.8273 ± 0.1190 |
| Ramachandran statistics (% of all residues) | |
| Most favored | 81.74 ± 2.59 |
| Additionally allowed | 14.91 ± 3.05 |
| Generously allowed | 1.76 ± 1.03 |
| Disallowed | 1.56 ± 1.23 |

[a] Final X-PLOR force constants were 250 (bonds), 250 (angles), 300 (impropers), 100 (chirality) and 100 (omega), 50 (NOE constraints), and 200 (torsion angle constraints).
[b] Nonbonded energy was calculated in XPLOR-NIH.
[c] The largest NOE violation in the ensemble of structures was 0.355 Å.
[d] The largest torsion angle violations in the ensemble of structures was 3.9°.

TABLE 2

Statistics for the 20 CXCL12-$\alpha_2$ L36C A65C with CXCR4 P38 C28A conformers

| Experimental constraints | |
|---|---|
| Distance constraints | |
| Long | |
| Intra-subunit | 444 |
| Inter- CXCL12-$\alpha$ monomers | 110 |
| Intermolecular (CXCL12-$\alpha$ to peptide) | 92 |
| Medium [1 < (i − j) ≦ 5] | 238 |
| Sequential [(i − j) = 1] | 384 |
| Intraresidue [i = j] | 744 |
| Total | 2012 |
| Dihedral angle constraints ($\phi$ and $\psi$) | 128 |

TABLE 2-continued

Statistics for the 20 CXCL12-$\alpha_2$ L36C A65C with CXCR4 P38 C28A conformers

| Average atomic R.M.S.D. to the mean structure (Å) | |
|---|---|
| Residues [a] | |
| Chemokine Backbone (C$^\alpha$, C', N) | 0.71 ± 0.07 |
| Chemokine Heavy atoms | 1.24 ± 0.10 |
| Total Backbone (C$^\alpha$, C', N) | 1.80 ± 0.24 |
| Total Heavy atoms | 2.26 ± 0.20 |
| Deviations from idealized covalent geometry [b] | |
| Bond lengths RMSD (Å) | 0.017 |
| Torsion angle violations RMSD (°) | 1.5 |
| WHATCHECK quality indicators | |
| Z-score | −3.47 ± 0.32 |
| RMS Z-score | |
| Bond lengths | 0.81 ± 0.03 |
| Bond angles | 0.79 ± 0.03 |
| Bumps | 0 ± 0 |
| Lennard-Jones energy [c] (kJ mol$^{-1}$) | −4620.1 ± 142.7 |
| Constraint violations [d] | |
| NOE distance Number > 0.5 Å | 0 ± 0 |
| NOE distance RMSD (Å) | 0.0276 ± 0.0017 |
| Torsion angle violations Number > 5° | 0.1 ± 0.45 |
| Torsion angle violations RMSD (°) | 0.8400 ± 0.1693 |
| Ramachandran statistics (% of all residues) | |
| Most favored | 71.30 ± 3.37 |
| Additionally allowed | 23.25 ± 3.08 |
| Generously allowed | 3.10 ± 1.09 |
| Disallowed | 2.38 ± 1.34 |

[a] 20 structure in the ensemble were aligned using residues 9-43 and 47-66 of the chemokine and 11-27 or the peptide. Chemokine RMSD includes residues 9-43, 47-66. Total RMSD includes the chemokine residues plus peptide residues 11-27.
[b] Final X-PLOR force constants were 250 (bonds), 250 (angles), 300 (impropers), 100 (chirality) and 100 (omega), 50 (NOE constraints), and 200 (torsion angle constraints).
[c] Nonbonded energy was calculated in XPLOR-NIH.
[d] The largest NOE violation in the ensemble of structures is Å.

TABLE 3

Statistics for the 20 CXCL12-$\alpha_2$ L36C A65C with sY21 CXCR4 P38 C28A conformers

| Experimental constraints | |
|---|---|
| Distance constraints | |
| Long | |
| Intra-subunit | 418 |
| Inter- CXCL12-$\alpha$ monomers | 116 |
| Intermolecular (CXCL12-$\alpha$ to peptide) | 92 |
| Medium [1 < (i − j) ≦ 5] | 246 |
| Sequential [(i − j) = 1] | 470 |
| Intraresidue [i = j] | 728 |
| Total | 2070 |
| Dihedral angle constraints ($\phi$ and $\psi$) | 128 |
| Average atomic R.M.S.D. to the mean structure (Å) | |
| Residues [a] | |
| Chemokine Backbone (C$^\alpha$, C', N) | 0.60 ± 0.10 |
| Chemokine Heavy atoms | 1.05 ± 0.11 |
| Total Backbone (C$^\alpha$, C', N) | 0.82 ± 0.09 |
| Total Heavy atoms | 1.37 ± 0.10 |
| Deviations from idealized covalent geometry [b] | |
| Bond lengths RMSD (Å) | 0.018 |
| Torsion angle violations RMSD (°) | 1.6 |
| WHATCHECK quality indicators | |
| Z-score | −3.34 ± 0.21 |
| RMS Z-score | |
| Bond lengths | 0.83 ± 0.02 |
| Bond angles | 0.83 ± 0.03 |

TABLE 3-continued

Statistics for the 20 CXCL12-$\alpha_2$ L36C
A65C with sY21 CXCR4 P38 C28A conformers

| | |
|---|---|
| Bumps | 0 ± 0 |
| Lennard-Jones energy [c] (kJ mol$^{-1}$) | −4640.2 ± 199.2 |
| Constraint violations [d] | |
| NOE distance Number > 0.5 Å | 0 ± 0 |
| NOE distance RMSD (Å) | 0.0324 ± 0.0016 |
| Torsion angle violations Number > 5° | 0.0 ± 0.0 |
| Torsion angle violations RMSD (°) | 0.7907 ± 0.1300 |
| Ramachandran statistics (% of all residues) | |
| Most favored | 70.21 ± 2.72 |
| Additionally allowed | 24.29 ± 2.80 |
| Generously allowed | 3.71 ± 1.18 |
| Disallowed | 1.74 ± 1.02 |

[a] 20 structure in the ensemble were aligned using residues 9-43 and 47-66 of the chemokine and 11-27 or the peptide. Chemokine RMSD includes residues 9-43, 47-66. Total RMSD includes the chemokine residues plus peptide residues 11-27.
[b] Final X-PLOR force constants were 250 (bonds), 250 (angles), 300 (impropers), 100 (chirality) and 100 (omega), 50 (NOE constraints), and 200 (torsion angle constraints).
[c] Nonbonded energy was calculated in XPLOR-NIH.
[d] The largest NOE violation in the ensemble of structures was 0.47 Å.

TABLE 4

Statistics for the 20 CXCL12-$\alpha_2$ L36C A65C
with sY7-12-21 CXCR4 P38 C28A conformers.

| | |
|---|---|
| Experimental constraints | |
| Distance constraints | |
| Long | |
| Intra-subunit | 420 |
| Inter- CXCL12-$\alpha$ monomers | 116 |
| Intermolecular (CXCL12-$\alpha$ to peptide) | 86 |
| Medium [1 < (i − j) ≤ 5] | 238 |
| Sequential [(i − j) = 1] | 456 |
| Intraresidue [i = j] | 722 |
| Total | 2092 |
| Dihedral angle constraints ($\phi$ and $\psi$) | 128 |
| Average atomic R.M.S.D. to the mean structure (Å) | |
| Residues [a] | |
| Chemokine Backbone (C$^\alpha$, C', N) | 0.64 ± 0.07 |
| Chemokine Heavy atoms | 1.10 ± 0.09 |
| Total Backbone (C$^\alpha$, C', N) | 1.01 ± 0.16 |
| Total Heavy atoms | 1.56 ± 0.017 |
| Deviations from idealized covalent geometry [b] | |
| Bond lengths RMSD (Å) | 0.017 |
| Torsion angle violations RMSD (°) | 1.5 |
| WHATCHECK quality indicators | |
| Z-score | −3.60 ± 0.25 |
| RMS Z-score | |
| Bond lengths | 0.78 ± 0.02 |
| Bond angles | 0.80 ± 0.02 |
| Bumps | 0 ± 0 |
| Lennard-Jones energy [c] (kJ mol$^{-1}$) | −4766.8 ± 145.4 |
| Constraint violations [d] | |
| NOE distance Number > 0.5 Å | 0 ± 0 |
| NOE distance RMSD (Å) | 0.0260 ± 0.0017 |
| Torsion angle violations Number > 5° | 0 ± 0 |
| Torsion angle violations RMSD (°) | 0.7380 ± 0.1314 |
| Ramachandran statistics (% of all residues) | |
| Most favored | 74.03 ± 2.65 |
| Additionally allowed | 22.13 ± 2.70 |
| Generously allowed | 2.15 ± 1.01 |
| Disallowed | 1.72 ± 1.22 |

[a] 20 structure in the ensemble were aligned using residues 9-43 and 47-66 of the chemokine and 11-27 or the peptide. Chemokine RMSD includes residues 9-43, 47-66. Total RMSD includes the chemokine residues plus peptide residues 11-27.
[b] Final X-PLOR force constants were 250 (bonds), 250 (angles), 300 (impropers), 100 (chirality) and 100 (omega), 50 (NOE constraints), and 200 (torsion angle constraints).
[c] Nonbonded energy was calculated in XPLOR-NIH.
[d] The largest NOE violation in the ensemble of structures was 0.407 Å.

The Protein Data Bank (PDB), under accession numbers 2K01, 2K04, 2K03 and 2K05 contain coordinates for these structural models. Restraints employed for structure determination have been deposited in the Biological Magnetic Resonance Bank, accession numbers 15633, 15636, 15635 and 15637. Standard calcium flux assays were used for testing CXCR4 activation and transwell chemotaxis assays were used to compare the chemotactic response of THP-1 cells towards wild-type CXCL12-$\alpha$, CXCL12-$\alpha$ H25R and CXCL12-$\alpha_2$. THP-1 cells are a CXCR4-expressing monocyte leukemia cell line and were obtained from ATCC.

EXAMPLE 2

Preparing the CXCL12-$\alpha_2$ Locked Dimer Polypeptide

In this Example, the inventors prepared the CXCL12-$\alpha_2$ locked dimer structure. Guided by the CXCL12-$\alpha$ crystal structure, the inventors identified L36 and A65 as residues at the dimer interface that could be replaced with intermolecular disulfide bonds (FIG. 1A). The CXCL12-$\alpha$ (L36C/A65C) double mutant was expressed and purified from E. coli as previously described for wild-type CXCL12-$\alpha$, and migrated as a stable dimer in non-reducing SDS-PAGE (FIG. 1B). Pulsed-field gradient NMR diffusion measurements indicated that CXCL12-$\alpha$ (L36C/A65C) is dimeric, even in solution conditions that favor the monomeric state (FIG. 1C).

Figure 2:
FIG. 2. CXCR4 N-terminus binds CXCL12-$\alpha_2$ (L36C/A65C) (CXCL12-$\alpha_2$). A) Ensemble of 20 CXCL12-$\alpha_2$ NMR solution structures (gray and tan) superimposed on the crystal structure of dimeric wild-type CXCL12-$\alpha$ (blue, PDB ID 2J7Z) with an $\alpha$-carbon RMSD of 1.2 Å for residues 9-66. Intermolecular C36-C65 disulfide bonds are shown in yellow. Flexible N-terminal residues of CXCL12-$\alpha$ (residues 1-8) are omitted for clarity. Refinement statistics for the CXCL12-$\alpha_2$ structure ensemble are given in table S1. B) $^{15}$N-$^1$H HSQC spectra of 25 µM [U-$^{15}$N]-CXCL12-$\alpha_2$ alone (black contours) and after addition of 100 µM p38 peptide (green contours). C) Combined $^{15}$N-$^1$H chemical shift perturbations plotted versus CXCL12-$\alpha_2$ residue number. Secondary structure elements are indicated and regions involved in the dimer interface are highlighted in orange. Missing values correspond to prolines (sequence positions 2, 10, 32 and 53) or amino acids not observed in the $^{15}$N-$^1$H HSQC spectra.
Figure 2:
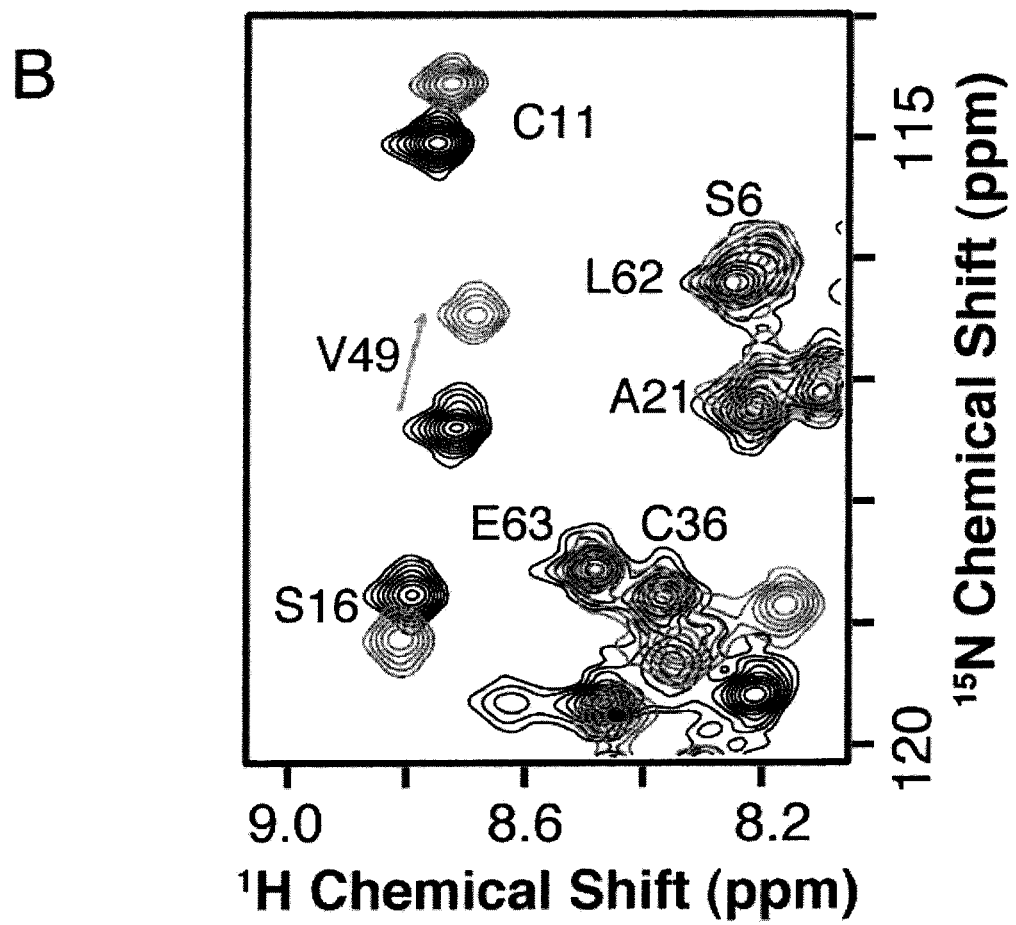
Figure 2:
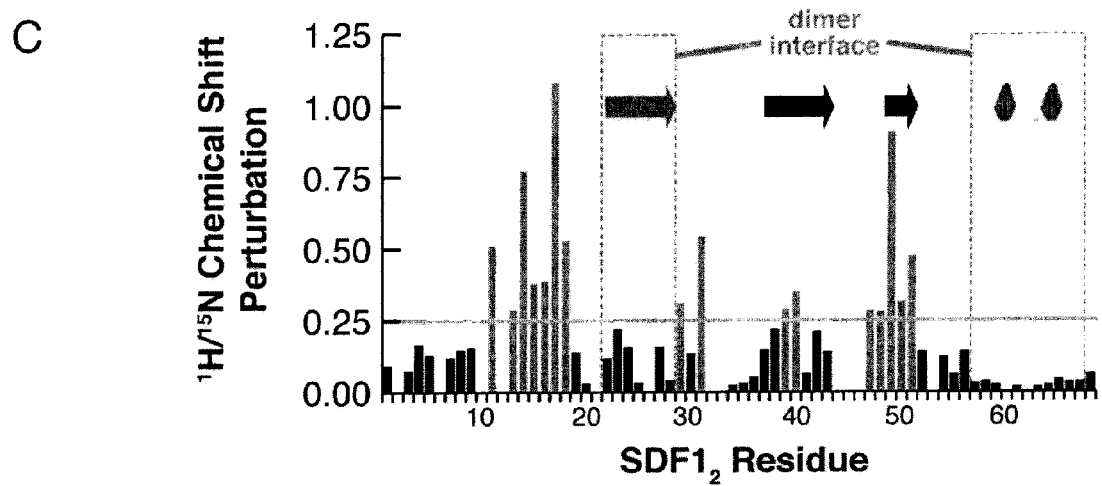

The inventors confirmed the presence of disulfide bonds linking the two monomers and solved the structure of the CXCL12-$\alpha_2$ (L36C/A65C) by NMR. The covalently-locked, symmetric CXCL12-$\alpha$ (L36C/A65C) dimer (CXCL12-$\alpha_2$) is superimposable with the wild-type CXCL12-$\alpha$ dimer observed crystallographically (FIG. 2A). Table 1 lists refinement statistics for the CXCL12-$\alpha_2$ structure ensemble. CXCL12-$\alpha_2$ also displays the canonical chemokine fold in which a flexible N-terminus is connected by the N-loop to a three-stranded antiparallel $\beta$-sheet and a C-terminal $\alpha$-helix.

EXAMPLE 3

Detection of 2:1 p38: CXCL12-$\alpha_2$ Binding by NMR Chemical Shift Mapping

In this Example, the inventors determined if the NMR broadening arises from exchange between different CXCL12-$\alpha$:p38 complexes. Previously, the inventors noted that binding of p38 (FIG. 5D) to $^{15}$N labeled CXCL12-$\alpha$ induced chemical shift perturbations attributable to a combination of CXCL12-$\alpha$ dimer formation and peptide binding. Titration of $^{15}$N p38 with CXCL12-$\alpha$ showed extreme line broadening. Based on the inventors' studies of the CXCL12-$\alpha$ monomer-dimer equilibrium, the inventors investigated that the NMR broadening arises from exchange between different CXCL12-$\alpha$:p38 complexes.

When both CXCL12-α dimerization and p38 binding are considered, a complex set of coupled binding equilibria permits exchange between complexes with stoichiometries of 1:1, 1:2, 2:1 and 2:2. Because the locked dimer reduces the number of accessible states, interpretation of NMR spectra of CXCL12-α$_2$ upon p38 binding is straightforward. Titration of $^{15}$N labeled CXCL12-α$_2$ with p38 (FIG. 2B) perturbs NMR signals for N-loop residues but not the dimer interface (FIG. 2C), thus identifying likely CXCR4-CXCL12-α binding determinants. Because only one set of CXCL12-α$_2$ signals is observed during the p38 titration and addition of more than two molar equivalents of p38 induces no further chemical shift perturbations, the inventors concluded that a symmetric 2:1 p38:CXCL12-α$_2$ complex was formed.

EXAMPLE 4

Structure Analysis of CXCL12-α$_2$ Locked Dimer Sulfotyrosine Recognition Sites

In this Example, the inventors measured the EC$_{50}$ of each protein using a Ca$^{2+}$-flux assay on CXCR4-expressing THP-1 cells to assess the relative contribution of each sulfotyrosine to CXCL12-α:CXCR4 binding. The CXCL12-α:p38 interaction contributes only to binding affinity and receptor specificity, but not to CXCR4 activation. In contrast, a peptide consisting of CXCL12-α residues 1-8 can fully activate CXCR4 at micromolar concentrations. Since each CXCL12-α variant retains the native N-terminus, the EC$_{50}$ value reflects its affinity for CXCR4. Consequently, an amino acid substitution that alters the Ca$^{2+}$-flux EC$_{50}$ relative to wild-type CXCL12-α (3.6±1.4 nM) has necessarily disrupted an interaction between the chemokine and the N-terminus or extracellular loops of CXCR4. Overall, mutations in wild-type CXCL12-α that alter interactions observed in the CXCL12-α$_2$:p38 complexes resulted in higher EC$_{50}$ values for CXCR4 activation corresponding to a loss of CXCL12-α binding affinity (Table 5). However, comparison of the results for each binding site reveals a hierarchy among CXCR4 sulfotyrosines.

NOE constraints from valine 23 of one CXCL12-α$_2$ subunit position the sY7 O-sulfonate to form a favorable electrostatic interaction with a positively-charged arginine side chain (FIG. 4B), but replacing R20 with alanine in wild-type CXCL12-α produced no change in EC$_{50}$ (Table 5).

TABLE 5

CXCR4 activation by CXCL12-α mutants.

| | EC$_{50}$ (nM) | Folded | Fold Increase | p38 contact |
|---|---|---|---|---|
| CXCL12-α | 3.6 ± 1.4 | + | | |
| R20A | 4.3 ± 0.6 | + | 1.2 | + |
| V23A | NA | − | NA | + |
| H25R | 5.1 ± 0.9 | + | 1.4 | − |
| K27A | 10.1 ± 2.9 | + | 2.8 | + |
| K27E | 16.8 ± 1.1 | + | 4.7 | + |
| V39A | 27.1 ± 0.2 | + | 7.5 | + |
| R41A | 4.3 ± 0.9 | + | 1.2 | − |
| R47A | 14.1 ± 0.6 | + | 3.9 | + |
| R47E | 654 ± 93 | + | 181.7 | + |
| V49A | 8.6 ± 2.4 | + | 2.4 | + |
| E60A | 4.1 ± 0.1 | + | 1.1 | − |
| E63A | 3.7 ± 0.8 | + | 1.0 | − |
| K64A | 5.0 ± 1.1 | + | 1.4 | − |

In a similar fashion, NOEs connect sY12 to P10 and L29 of the other CXCL12-α$_2$ subunit and place the sulfotyrosine within approximately 3 Å of the positively charged amino group of K27 (FIG. 4C). Substitutions of alanine and glutamic acid at this position in wild-type CXCL12-α increased the EC$_{50}$ to 10.1 and 16.8 nM, respectively. Alanine substitution of a structurally adjacent valine residue (V39A) increased the EC$_{50}$ to 27.1 nM.

Residues connecting the N-terminal CXC motif with β1 of CXCL12-α (the 'N loop'), particularly the RFFESH motif consisting of residues 12-17, were predicted from mutagenic studies to interact with the CXCR4 N-terminus. The inventors observed intermolecular NOEs between $^1$H$^N$ of F14 in CXCL12-α$_2$ and the $^1$H$^α$ of G19 from CXCR4 and from V18 in the chemokine to sY21. NOEs also link sY21 with V49, located in the β3 strand of CXCL12-α$_2$, and position the sY21 O-sulfonate <5 Å from the R47 guanidinium (FIG. 4D), consistent with our earlier measurement of sulfotyrosine-specific chemical shift perturbations. CXCL12-α R47A has an EC$_{50}$ of 14.1 nM, and replacement of the positive arginine side chain with a negatively charged glutamic acid drastically alters CXCL12-α binding (R47E EC$_{50}$=654 nM) relative to wild-type CXCL12-α (EC$_{50}$=3.6 nM).

The level of sulfation for each CXCR4 tyrosine has not been characterized in THP-1 cells, but Farzan et al. suggested that CXCR4 Y21 is sulfated to higher degree than Y7 or Y12 and that sY21 contributes the most to CXCL12-α binding affinity. This is consistent with the results herein which suggest the sY7 and sY12 binding sites contribute only modestly to the overall interaction. The binding pocket for sY21 in CXCL12-α appears to be well conserved within the CXC chemokine family with 8 out of 16 CXC chemokines showing high conservation or identity at CXCL12-α positions 18, 47 and 49. With the exception of CXCR6, a tyrosine corresponding to sulfotyrosine 21 of CXCR4 appear to be present in all receptors of the CXC family. Neither sY7, sY12 nor their putative binding sites are conserved in the CXC ligands or receptors.

EXAMPLE 5

Structure of CXCL12-α$_2$ Locked Dimer Bound to Sulfated p38 Peptides

In this Example, the inventors solved structures of unsulfated, selectively sulfated and fully sulfated CXCR4 peptides bound to the CXCL12-α$_2$ locked dimer polypeptide to understand the role of sulfotyrosine in CXCL12-α-CXCR4 binding.

Tyrosine sulfation in the CXCR4 N-terminal domain contributes substantially to CXCL12-α binding. The inventors showed previously that sulfation of Tyr 21 enhances the affinity of p38 for CXCL12-α by approximately 3-fold, and the inventors observed that fully-sulfated p38-sY$_3$ binds approximately 20-fold more tightly than the unsulfated peptide (apparent K$_d$=0.2±0.2 µM).

Figure 3:
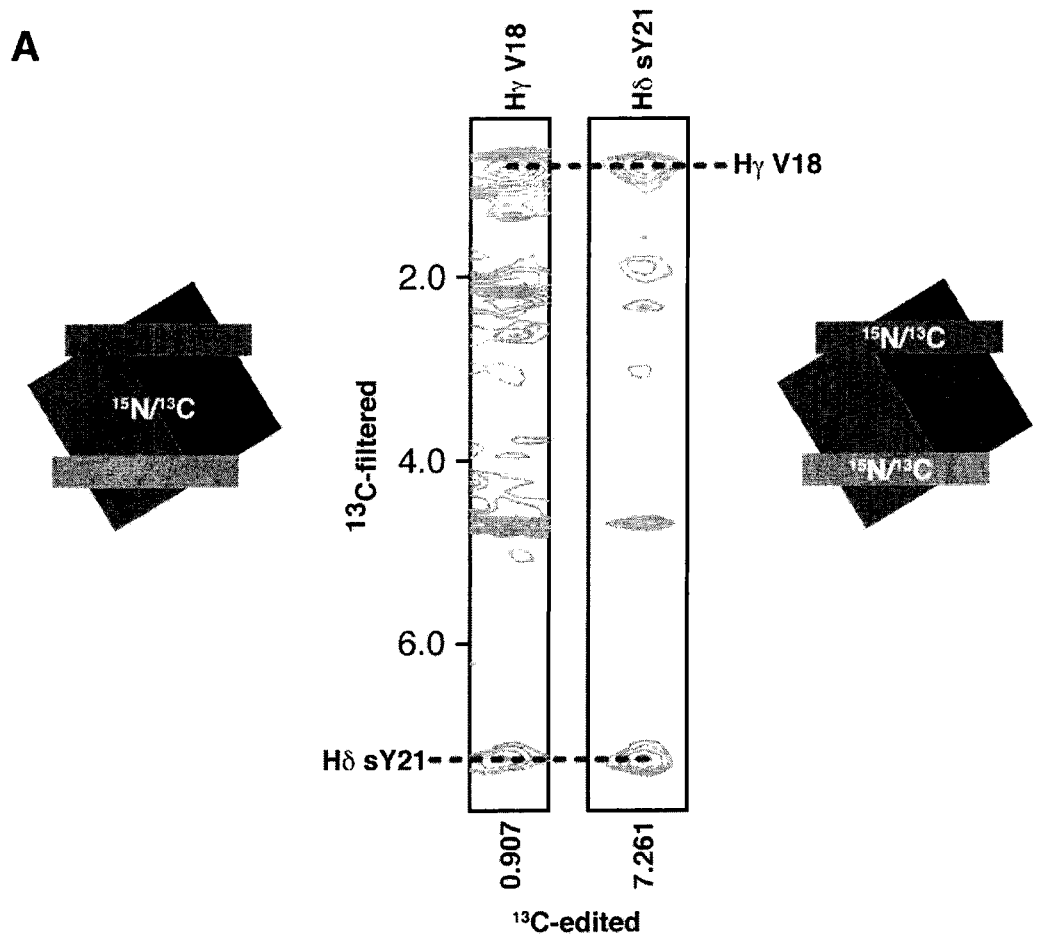
FIG. 3. CXCL12-$\alpha_2$ CXCR4 N-terminal domain structures. (A) Representative intermolecular NOEs for the CXCL12-$\alpha_2$:p38-sY$_1$ complex. Strips from 3D F1-$^{13}$C-filtered/F3-$^{13}$C-edited NOESY-HSQC spectra acquired on a complex containing [U-$^{15}$N,$^{13}$C]-CXCL12-$\alpha_2$ and unlabeled p38-sY$_1$ (left) and a complex containing [U-$^{15}$N,$^{13}$C]-p38-sY$_1$ and unlabeled CXCL12-$\alpha_2$ (right) contain equivalent NOEs between the V18 methyl of SDF1$_2$ and sY21 $^1$H$^\delta$ of p38-sY$_1$. Ensembles of the twenty lowest energy conformers for the (B) CXCL12-$\alpha_2$:p38, (C) CXCL12-$\alpha_2$:p38-sY$_1$, and (D) CXCL12-$\alpha_2$:p38-sY$_3$ complexes. CXCL12-$\alpha_2$ is shown in gray and the CXCR4 N-termini are orange. Sulfotyrosine residues in CXCR4 N-terminus are shown in red.
Figure 3:
Figure 3:
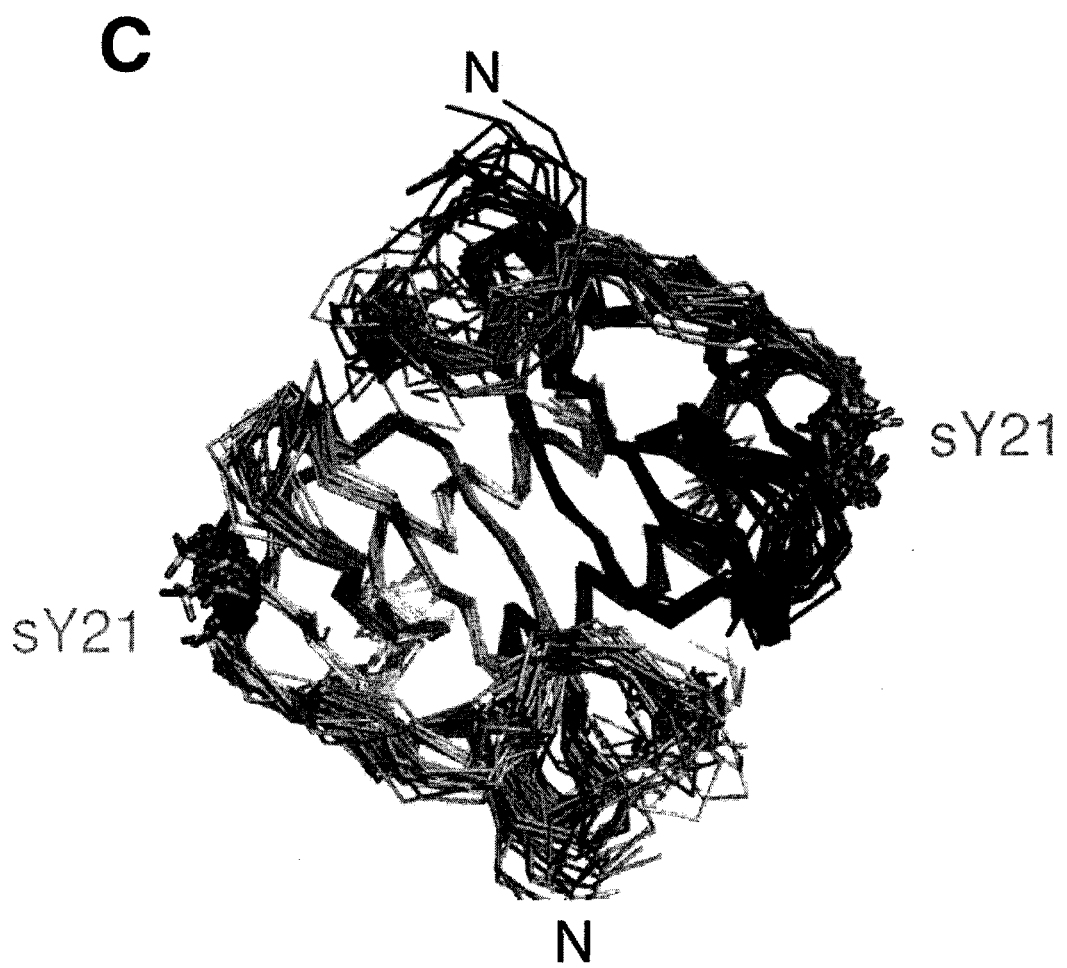
Figure 3:
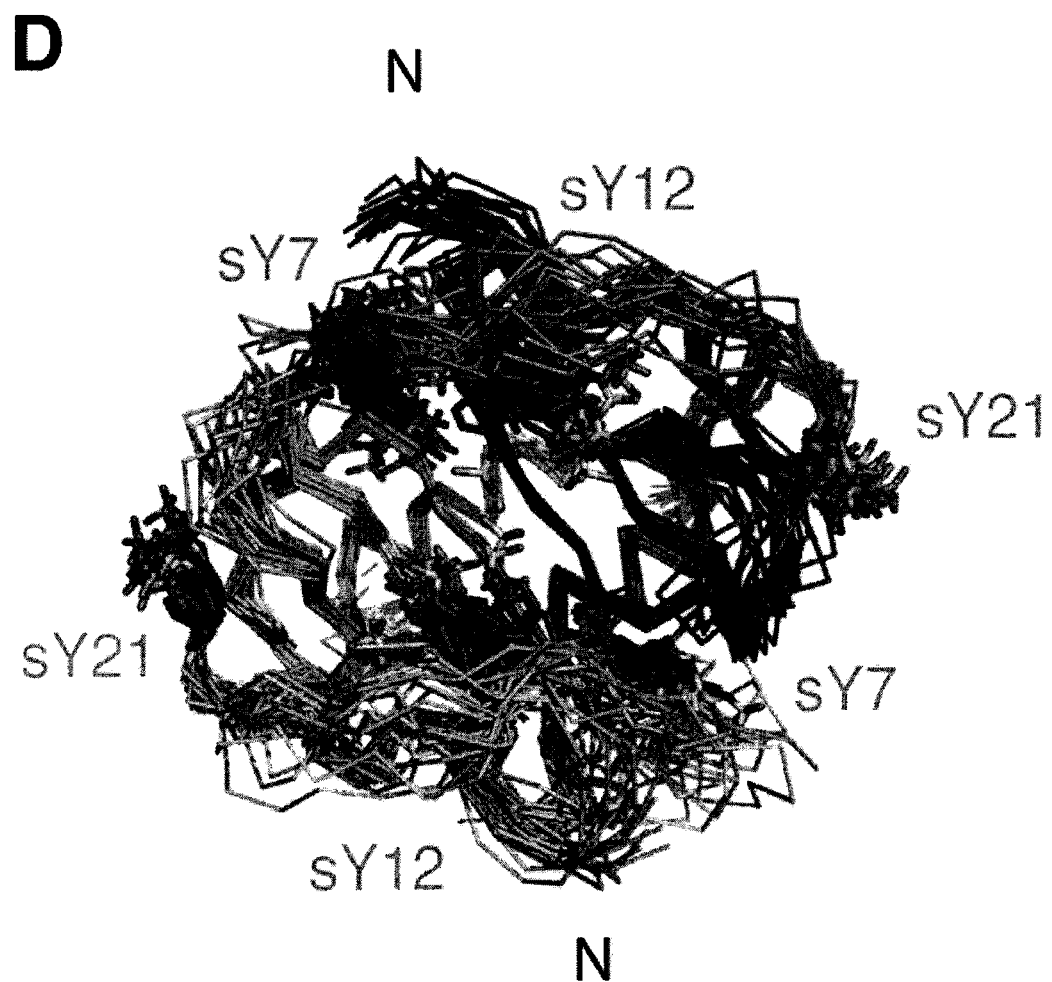

Recombinant [U-$^{15}$N,$^{13}$C]-labeled CXCR4 peptide (p38) was modified using purified tyrosyl protein sulfotransferase to contain sulfotyrosine at position 21 (p38-sY$_1$) or positions 7, 12 and 21 (p38-sY$_3$) (FIG. 1D). For each complex, NOEs between CXCL12-α$_2$ and the (sulfo)tyrosine side chains of CXCR4 unambiguously defined the same arrangement of both p38 peptides on the chemokine as shown in FIG. 3 with representative intermolecular NOEs in FIG. 1B.

Two p38 molecules bind in equivalent orientations with each peptide wrapping around the symmetric CXCL12-α$_2$ dimer in an extended conformation (FIG. 2D). When mapped onto the CXCL12-α$_2$ surface, p38-induced chemical shift perturbations (FIG. 2D, green surface) correlate strongly with the observed binding interface. In contrast, residues of the flexible N-terminus and C-terminal α-helix of CXCL12-$α_2$ were unperturbed by p38 binding and do not interact with the CXCR4 N-terminus.

CXCR4 stabilizes the CXCL12-α dimer by interacting with both subunits and recognizing unique features of the dimer interface. Near the CXCR4 N-terminus, each p38 peptide crosses the CXCL12-$α_2$ dimer interface, such that sY7 and sY12 interact with opposing CXCL12-α monomers. In the membrane-proximal portion of the CXCR4 N-terminal domain, P27 inserts between Q59 of one CXCL12-$α_2$ subunit and L66 of the opposing subunit, where the C-terminal helices from each monomer pack against each other.

EXAMPLE 6

Inhibitory Effect of CXCL12-$α_2$ Locked Dimer on Cell Migration

In this example, the inventors conducted chemotaxis assays using a C-CXCL12-α mutant that remains monomeric at higher concentrations than wild-type CXCL12-α. Since the dimer $K_d$ of CXCL12-α (H25R) is approximately 10-fold higher than wild-type, it should resist inactivation due to dimerization and maintain a chemotactic response at higher concentrations where the wild-type CXCL12-α loses activity. Both proteins induce a dose-dependent chemotactic response from 1-30 nM, but CXCL12-α (H25R) promotes cell migration much more strongly than the wild-type chemokine at higher concentrations (70-100 nM) before returning to baseline levels (FIG. 5C).

The inventors data shows that CXCL12-$α_2$ inhibits chemotaxis induced by wild-type CXCL12-α. FIG. 5D shows CXCL12-$α_2$ inhibits chemotaxis induced by wild-type CXCL12-α with an $IC_{50}$ of approximately 4 nM. The inventors' results show that monomer CXCL12-α activates cell migration while dimer CXCL12-α halts cell migration. The results also demonstrate that CXCL12-$α_2$ acts as a partial CXCR4 agonist (as evidenced by the detection of the secondary messenger calcium) and as a selective antagonist that blocks chemotaxis. This indicates CXCL12-$α_2$ can serve as a tool for correlating cellular responses with different intracellular signaling pathways initiated by CXCR4. Also, CXCL12-$α_2$ may be useful in the development of anti-metastatic agents by preventing CXCL12-α/CXCR4-mediated migration of circulating cancer cells.

EXAMPLE 7

Physiological Relevance of the CXCL12-$α_2$ Locked Dimer

In this Example, the inventors next investigated whether CXCL12-$α_2$ locked dimers participate in CXCR4 signaling. Like most chemokines, CXCL12-α self-association occurs well above the concentrations required for receptor binding and activation (1-10 nM). Consequently, chemokine dimers are considered relevant mainly in the context of glycosaminoglycan binding for immobilization in the extracellular matrix. Debate over the functional role of chemokine dimers in vivo is complicated by conflicting results obtained on a variety of the >40 different chemokine proteins.

The inventors monitored activation of CXCR4 using THP-1 cells and a similar $Ca^{2+}$-flux assay. Robust CXCR4 activation was observed with both wild-type CXCL12-α ($EC_{50}$=3.6 nM) and CXCL12-$α_2$ ($EC_{50}$=12.9 nM) (FIG. 5A). AMD3100, a small-molecule CXCR4 antagonist, inhibited both proteins with $IC_{50}$ values of 3.3 nM (CXCL12-A) and 3.2 nM (CXCL12-$α_2$), demonstrating that the observed calcium flux responses were mediated by CXCR4. Thus, the inventors data shows that CXCL12-$α_2$ binds and activates its cognate receptor.

EXAMPLE 8

Chemotactic Response of the CXCL12-$α_2$ Locked Dimer Polypeptide

In this Example, the inventors used standard transwell chemotaxis assays to compare the chemotactic response of THP-1 cells towards wild-type CXCL12-α and the CXCL12-$α_2$ locked dimer polypeptide of the present invention. As expected, the THP-1 cells responded chemotactically when exposed to wild-type CXCL12-α in the 1-30 nM range, but migration decreases and ultimately ceases at higher chemokine concentrations (FIG. 5B).

In contrast to wild-type CXCL12-α, the constitutively dimeric CXCL12-$α_2$ of the present invention failed to attract cells in a transwell chemotaxis assay even at concentrations up to 1 µM (FIG. 5B). Accordingly, the inventors results demonstrate that at low chemokine concentrations monomeric CXCL12-α stimulates chemotaxis, while at higher concentrations CXCL12-$α_2$ halts cell migration corresponding to the second, downward half of the bell-shaped curve (see Example 8).

EXAMPLE 9

Prophetic Example on the Inhibitory Effect of the CXCL12-$α_2$ Locked Dimer on Tumor Growth In this Example, the inventors describe how one would used the inhibitory effect of the CXCL12-$α_2$ locked dimer of the present invention to affect tumor growth. Primary tumors are easier to treat as compared to cancer which has spread through the body and formed secondary tumors or metastases. It has long been observed that secondary tumors in metastatic cancer patients form preferentially in a subset of tissues, including bone marrow, lymph nodes, liver, and lungs. At least three theories have been proposed to explain these observations, including: certain tissues are better environments for metastatic cancer cell survival; the vasculature of some tissues express adhesion molecules that bind metastatic cells better than others; or there is active recruitment of metastatic cells out of the blood stream or lymphatic system only to certain locations.

Patterns of CXCR4 and CXCL12 expression and signaling suggest that metastatic cancer cells are actively recruited to tissues producing CXCL12. An increase in CXCR4 expression accompanies the transition from a primary tumor cell to a metastatic cancer cell, and CXCR4 levels have been correlated with metastasis and poor patient outcomes in many different cancer types. These metastatic, CXCR4-expressing cancer cells break away from the primary tumor and enter the circulation where they systematically target tissues constitutively expressing CXCL12, the only natural ligand for CXCR4, like bone marrow, lymph nodes, liver, and lungs. It is thought that this targeting occurs in a manner analogous to the recruitment of a circulating leukocyte to an infection site.

CXCL12- and CXCR4-directed localization of metastatic cancer cells has been implicated in a broad range of over twenty cancer types, including: breast, prostate, colon, myeloma, melanoma, tongue, ovarian, small and non-small cell lung cancers, pancreatic, esophageal, head and neck, bladder, osteosarcoma, neuroblastoma, and leukemia.

The inventors have shown that the CXCL12-$\alpha_2$ locked dimer of the present invention is a potent inhibitor of CXCL12/CXCR4 mediated chemotaxis of a THP1 cells (a leukemia cell line) (FIG. 5E). This CXCL12/CXCR4 mediated chemotaxis or cell migration is required for CXCL12/CXCR4 directed cancer metastasis. Based on the potent inhibition of CXCL12 induced THP1 cell chemotaxis by CXCL12-$\alpha_2$, the inventors predict that the CXCL12-$\alpha_2$ locked dimer of the present invention will prevent CXCL12-induced chemotaxis (or cell migration) and thus metastasis of cancer cells that express CXCR4. The inventors therefore predict that blockade of the CXCL12/CXCR4-directed metastasis with the CXCL12-$\alpha_2$ locked dimer of the present invention will prevent or reduce the formation of secondary tumors or metastases. For example, a person diagnosed with breast cancer could be treated with CXCL12-$\alpha_2$ to prevent metastasis before and after surgical removal of the primary tumor. Continued CXCL12-$\alpha_2$ administration could improve the efficacy of subsequent chemotherapy or radiation treatments by preventing circulating cancer cells from migrating to tissues and organs that would normally serve as a preferred location for metastatic cancer growth. The inventors predict that fewer recurrences or metastases would occur after a successful initial treatment of breast cancer. Pancreatic cancer has a high mortality rate and kills quickly, largely because pancreatic cancer metastasizes rapidly in a CXCL12/CXCR4 dependant manner. In a manner analogous to breast cancer the inventors predict that treatment with CXCL12-$\alpha_2$ would increase the life expectancy of a patient with pancreatic cancer by slowing the spread of metastatic disease.

EXAMPLE 10

Prophetic Example on the Inhibitory Effect of the CXCL12-$\alpha_2$ Locked Dimer on Angiogenisis In this example, the inventors show how one would use the inhibitory effect of the CXCL12-$\alpha_2$ locked dimer of the present invention to inhibit angiogenesis. Angiogenesis is the formation of new blood vessels that penetrate a tissue and supply that tissue with oxygen and nutrients while also removing waste. Usually the formation of new blood vessels results from expansion or growth of existing blood vessels through the growth of vascular endothelial cells. The vascular endothelial cells that line blood vessels rarely divide but there are cues that can induce or inhibit growth. When the expansion cues outweigh the inhibiting cues, angiogenesis occurs.

CXCL12 expression is increased in tissues that are hypoxic (or lack oxygen) due to a lack of vascularization (or lack of blood vessels and blood supply). CXCL12 is also a chemoattractant that functions to attract the newly forming blood vessels into the hypoxic tissue. Angiogenesis is important for the progression of numerous disease states and inhibition of angiogenesis by CXCL12$\alpha_2$ may be therapeutically useful in the prevention or progression of diseases conditions including but not limited to diabetic retinopathy, macular degeneration, rheumatoid arthritis, inflammatory bowel disease, cancer, psoriasis, osteoarthritis, ulcerative colitis, Crohn's disease and coronary thrombosis.

EXAMPLE 11

Prophetic Example on the Inhibitory Effect of the CXCL12-$\alpha_2$ Locked Dimer on Autoimmune Diseases In this example, the inventors show how one would use the inhibitory effect of the CXCL12-$\alpha_2$ locked dimer of the present invention to inhibit autoimmune diseases.

Autoimmune diseases occur when a body's immune system attacks its own cells and tissues in addition to or instead of things foreign. CXCL12 is a chemokine and like other chemokines is involved in regulating immune cell trafficking and the immune system in general. As such, CXCL12 plays roles in recruiting immune cells during an autoimmune reaction. Rheumatoid arthritis is an example of such an autoimmune disease. In rheumatoid arthritis CXCL12 recruits T-cells to joints where the recruited T-cells orchestrate the generation of immunologically driven inflammation. Therefore, preventing the migration and recruitment of T-cells to the synovium of joints with the CXCL12$\alpha_2$ locked dimer of the present invention may prevent or reduce the inflammation associated with rheumatoid arthritis.

EXAMPLE 12

Prophetic Example on the Inhibitory Effect of the CXCL12-$\alpha_2$ Locked Dimer on HIV/AIDS In this example, the inventors show how one would use the inhibitory effect of the CXCL12-$\alpha_2$ locked dimer of the present invention to inhibit HIV/AIDS. In this example, the inventors show how one would also evaluate the effect of combination therapies using the inhibitory effect of the CXCL12-$\alpha_2$ locked dimer of the present invention to treat HIV/AIDS.

Human immunodeficiency virus (HIV) is a retrovirus that can lead to acquired immunodeficiency syndrome (AIDS), a condition in humans in which the immune system begins to fail, leading to life-threatening opportunistic infections. Infection with HIV occurs by the transfer of contaminated bodily fluids such as blood, semen, vaginal fluid, pre-ejaculate, or breast milk. Within these bodily fluids, HIV is present as both free virus particles and virus within infected immune cells. CXCR4 and/or CCR5 along with CD4 are coreceptors that HIV uses when infecting cells. There are different strains of HIV. R5 strains use CCR5 and CD4 as coreceptors to infect macrophages. X4 strains use CXCR4 and CD4 to gain entrance into T cells while dual tropic HIV strains can use either CXCR4 or CCR5 along with CD4 as coreceptors when infecting cells.

HIV primarily infects vital cells in the human immune system such as helper T cells (specifically $CD4^+$ T cells), macrophages and dendritic cells. HIV infection leads to low levels of $CD4^+$ T cells through three main mechanisms: firstly, direct viral killing of infected cells; secondly, increased rates of apoptosis in infected cells; and thirdly, killing of infected $CD4^+$ T cells by CD8 cytotoxic lymphocytes that recognize infected cells. When $CD4^+$ T cell numbers decline below a critical level, cell-mediated immunity is lost, and the body becomes progressively more susceptible to opportunistic infections. If untreated, eventually most HIV-infected individuals develop AIDS (Acquired Immunodeficiency Syndrome) and die; however about one in ten remains healthy for many years, with no noticeable symptoms. Treatment with anti-retrovirals, where available, increases the life expectancy of people infected with HIV.

Based on the inhibitory effect of the CXCL12-$\alpha_2$ locked dimer of the present invention, the inventors predict that the CXCL12-$\alpha_2$ locked dimer would be effective in blocking the entry of HIV-1 into human T cells. Certain strains of HIV (X4 or dual tropic) utilize CXCR4 as a co-receptor, and this interaction is critical for fusion of the viral and T cell membranes in the process of HIV entry. By binding to CXCR4 and preventing it from serving as a viral coreceptor, the wild-type CXCL12-$\alpha$ chemokine inhibits HIV entry with an $IC_{50}$ of 79 nM (9, 38). Accordingly, the inventors predict that the CXCL12-$\alpha_2$ locked dimer of the present invention will be more effective at lower concentrations since it should block the CXCR4 receptor more completely than the monomeric, wild-type chemokine. Additionally, the inventors predict the CXCL12-$\alpha_2$ locked dimer will work synergistically or additively with HAART, a combination therapy, or other current HIV/AIDS treatments.

EXAMPLE 13

Prophetic Example of the Inhibitory Effect of the CXCL12$\alpha_2$ Locked Dimer on Blood Cancers In this example, the inventors show how one would use the inhibitory effect of the CXCL12-$\alpha_2$ locked dimer of the present invention to treat blood cancers.

Figure 5:
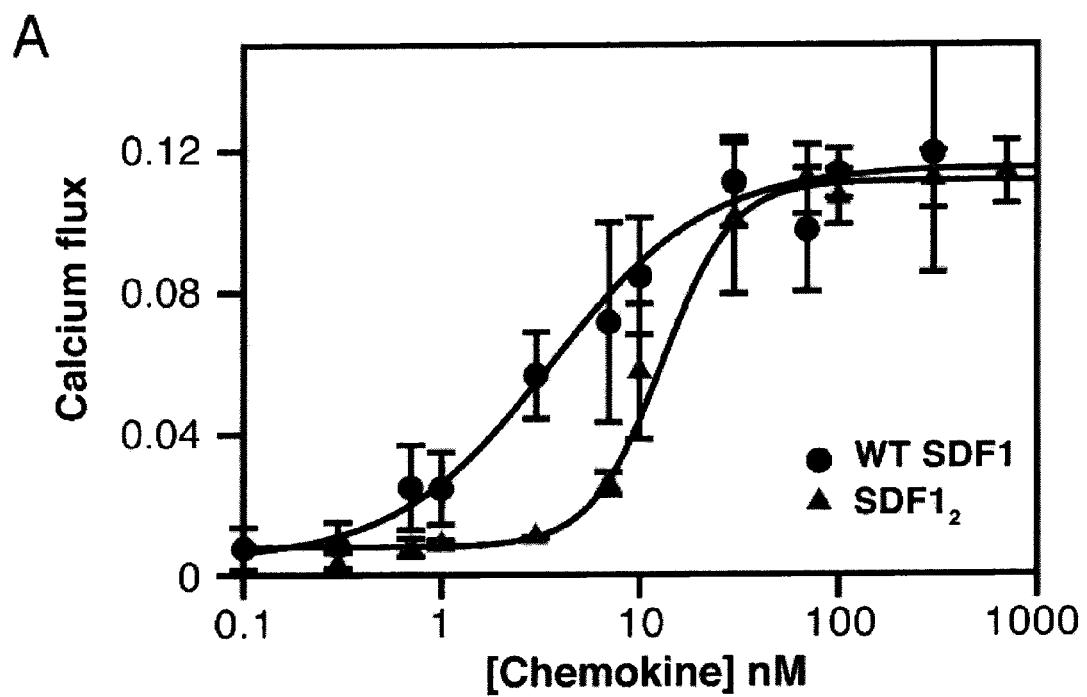
FIG. 5. Dimeric CXCL12-$\alpha_2$ induces CXCR4-mediated Ca$^{2+}$-flux but inhibits chemotaxis toward monomeric wild-type CXCL12-$\alpha$. A) Ca$^{2+}$-flux in THP-1 cells loaded with Fluo-3 (Invitrogen) indicates robust dose-dependant CXCR4 activation by wild-type CXCL12-$\alpha$ (●, EC$_{50}$=3.6 nM) and CXCL12-$\alpha_2$ (▲, EC$_{50}$=12.9 nM). B) Wild-type CXCL12-$\alpha$ chemoattracts THP-1 cells in a biphasic, concentration-dependent manner with maximal migratory response at ~30 nM. In contrast, CXCL12-$\alpha_2$ does not chemoattract THP-1 cells at all protein concentrations from 1-1,000 nM. C) Schematic illustration of the bell-shaped profile for CXCL12-$\alpha$-mediated chemotaxis arising from changes in relative concentrations of chemokine monomer and dimer. At low chemokine concentration monomeric CXCL12-$\alpha$ promotes chemotaxis (green curve), while increasing CXCL12-$\alpha_2$ dimerization at high chemokine concentrations halts chemotaxis (red curve). D) Wild-type CXCL12-α and the dimerization-impaired H25R variant chemoattract THP-1 cells equally well at low concentrations (0.1-10 nM). CXCL12-α (H25R) remains monomeric at higher concentrations relative to wild-type CXCL12-α and induces chemotaxis over a broader range. E) Chemoattraction of THP-1 cells induced by 10 nM wild-type CXCL12-α is inhibited by CXCL12-α$_2$ (IC$_{50}$~4 nM).
Figure 5:
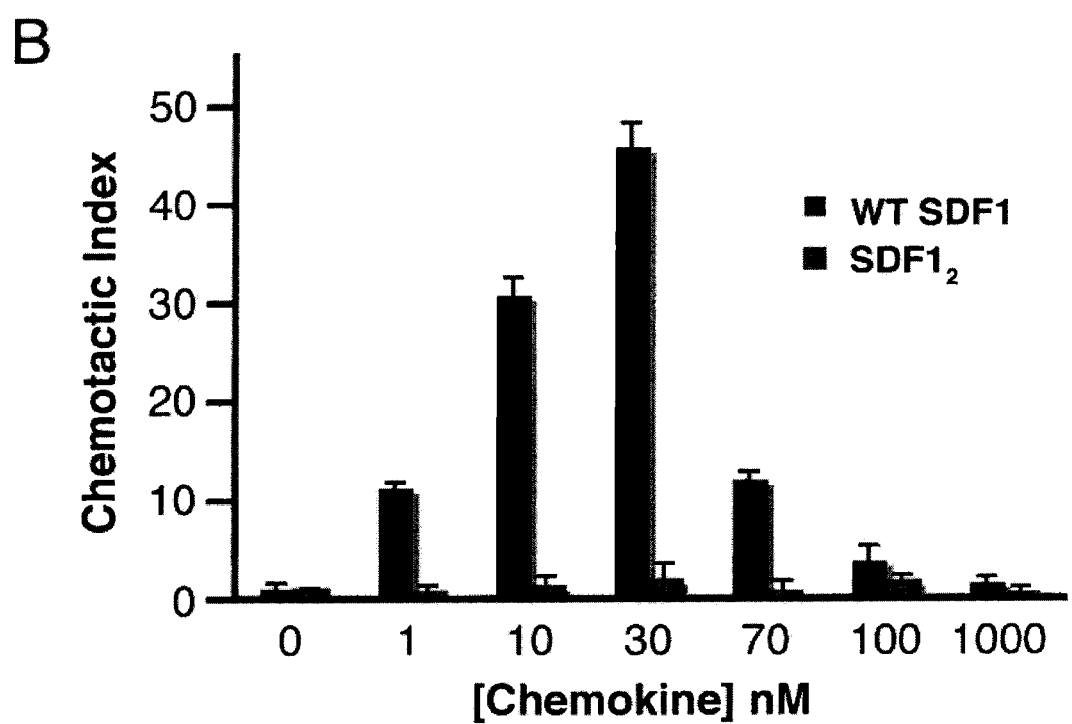
Figure 5:
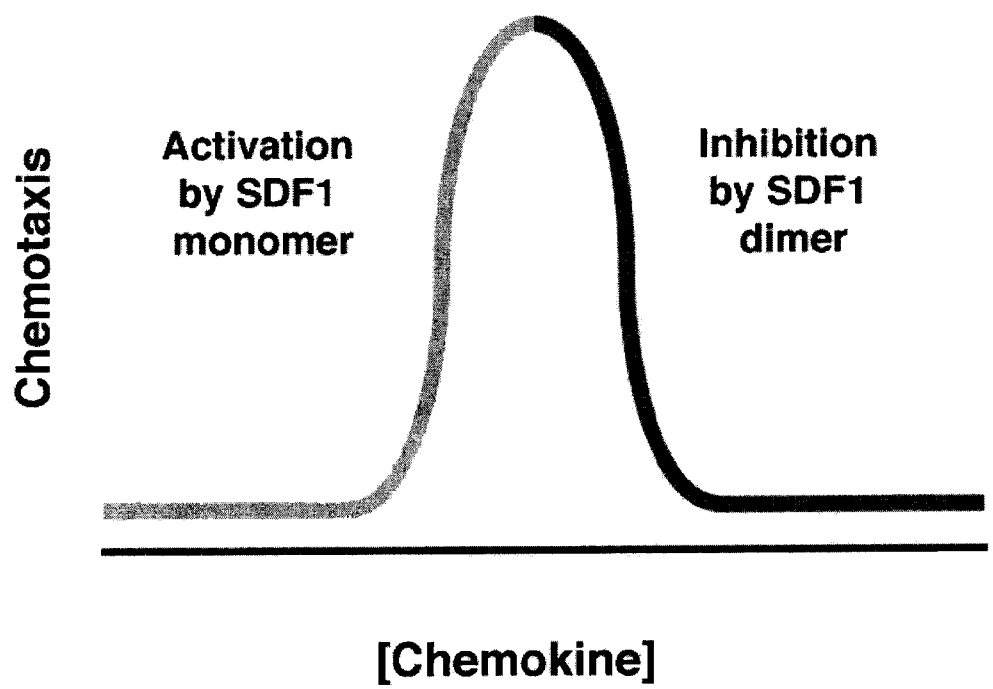
Figure 5:
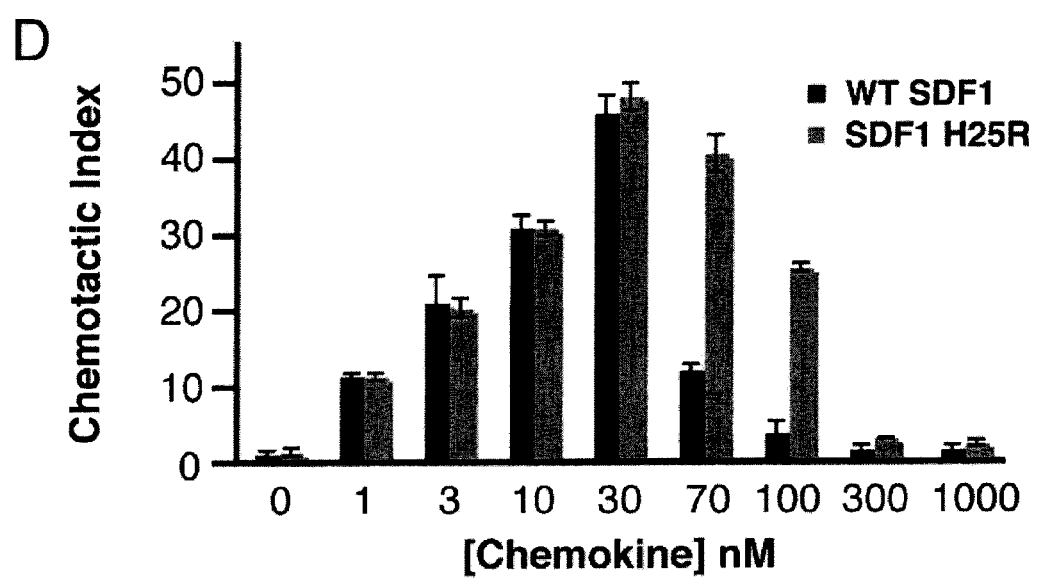
Figure 5:
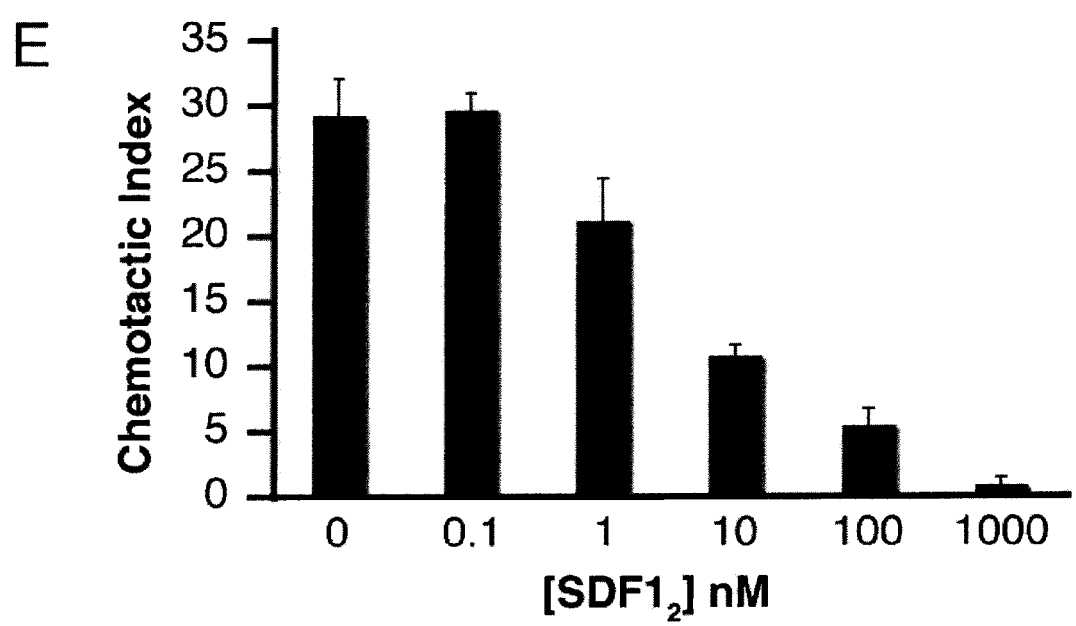

Blood cancers cells such as leukemia, lymphoma and myeloma that express CXCR4 are trafficked throughout the body in response to CXCL12. Blocking CXCR4 signaling can help prevent this trafficking, thus exposing these cancers to treatments, like chemotherapy, resulting in an enhanced effectiveness of the current therapy. CXCL12 traffics these cancers to the bone marrow, which provides a protective environment that enhances proliferation and anti-apoptotic signals that can result in the cancers being less sensitive to the therapies currently used. The inventors have shown that the CXCL12$\alpha_2$ locked dimer of the present invention inhibits migration of THP-1 cells, a leukemia cell line, toward CXCL12 (FIG. 5). Therefore, adding the CXCL12$\alpha_2$ locked dimer of the present invention to the current treatment of blood cancers, like leukemia, lymphoma and myeloma, will prevent the migration of these cancers into the bone marrow in response to the CXCL12 that is produced there. Thus, the cancer cells will not enter the protective bone marrow and will be more sensitive and responsive to the current cytotoxic therapeutics.

EXAMPLE 14

Prophetic Example of the Inhibitory Effect of the CXCL12$\alpha_2$ Locked Dimer on IBD In this example, the inventors show how one would use the inhibitory effect of the CXCL12-$\alpha_2$ locked dimer of the present invention to treat gastrointestinal inflammation associated with IBD.

By "gastrointestinal inflammation" we mean inflammation of a mucosal layer of the gastrointestinal tract, and encompass acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. By "chronic gastrointestinal inflammatory conditions" (also referred to as "chronic gastrointestinal inflammatory diseases") we mean, but are not necessarily limited to, inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), colitis in conditions such as chronic granulomatous disease, celiac disease, celiac sprue (a heritable disease in which the intestinal lining is inflamed in response to the ingestion of a protein known as gluten), food allergies, gastritis, infectious gastritis or enterocolitis (e.g., *Helicobacter pylori*-infected chronic active gastritis) and other forms of gastrointestinal inflammation caused by an infectious agent, and other like conditions.

By "inflammatory bowel disease" or "IBD" we mean any of a variety of diseases characterized by inflammation of all or part of the intestines. Examples of IBD include, but are not limited to, Crohn's disease and ulcerative colitis. Reference to IBD throughout the specification is often referred to in the specification as exemplary of gastrointestinal inflammatory conditions, and is not meant to be limiting.

Clinical and experimental evidence suggest that the pathogenesis of IBD is multifactorial involving susceptibility genes and environmental factors. The interaction of these factors with the immune system leads to intestinal inflammation and dysregulated mucosal immunity against commensal bacteria, various microbial products (e.g., LPS) or antigens. Animal models of colitis have highlighted the prominent role of CD4+ T cells in the regulation of intestinal inflammation. Cytokine imbalance, and the production of inflammatory mediators have been postulated to play an important role in the pathogenesis of both experimental colitis and IBD. In particular, dysregulated CD4+ T cell responses play a pivotal role in the pathogenesis of experimental colitis. Therefore, adding the CXCL12$\alpha_2$ locked dimer of the present invention to the current treatment of IBD will prevent the migration of these inflammatory mediators.

The invention provides a new and potent therapeutic advantage that is effective across species in a variety of animal models of chronic and/or acute gastrointestinal inflammation, particularly in animal models of IBD, which animal models are regarded in the field as models of disease in humans. In use, the composition and methods of the present invention will reduce disease activity, e.g., diarrhea, rectal bleeding and weight loss, reduce colon weight and colon lesions, as well as reduce colonic inflammation, as measured by, for example, anti-neutrophil cytoplasmic antibodies (ANCA), colonic myclo-peroxidase activity, or other conventional indicator of gastrointestinal inflammation.

EXAMPLE 15

Prophetic Example of the Effect of Combination Therapies Using the CXCL12$\alpha_2$ Locked Dimer on Cancer, Inflammation, Auto-Immune Diseases and/or HIV/AIDS In this example, the inventors show how one would evaluate the effect of combination therapies using the inhibitory effect of the CXCL12-$\alpha_2$ locked dimer of the present invention to treat cancer, inflammation, auto-immune diseases and/or HIV/AIDS.

For instance, the locked dimer of the present invention may be used as an agonist or antagonist in combination with other known anti-inflammatory, HIV, autoimmune or cancer therapies. By "agonist" we mean a ligand that stimulates the receptor the ligand binds to in the broadest sense. An "agonist" or an "antagonist" is a compound or composition that, respectively, either detectably increases or decreases the activity of a receptor, an enzyme or another biological molecule, which can lead to increased or decreased transcription or mRNA levels of a regulated gene or to another measurable effect such as altered level of activity of the gene product or protein. The increase or decrease in a receptor's or enzyme's activity will be an increase or a decrease of at least about 5%, 10%, 20%, 30%, 40%, 50%, 60%, 70%, 80%, 90%, 95% or a range about between any two of these values, for one or more measurable activities. Receptors, their accessory factors and associated transcription factors can modulate transcription of their target gene(s) by detectably increasing or decreasing transcription or mRNA levels. Biological activities of receptors may also include modulating biological responses such as signal transduction within a cell or ion flux, e.g., sodium, potassium or calcium, across cell or organelle membranes, e.g., across mitochondria.

The locked dimer of the present invention may also be used as a super-agonist. By "super-agonist", we mean a type of agonist that binds permanently to a receptor in such a manner that the receptor is permanently activated. It is distinct from a mere agonist in that the association of an agonist to a receptor is reversible, whereas the binding of an super-agonist to a receptor is, at least in theory, irreversible.

In use, the locked dimer of the present invention allows b-arrestin mediated receptor internalization and down-regulation. This is a major advantage of the dimer since the combination of antagonism with respect to CXCL12 induced migration AND ongoing CXCL12 dimer induced receptor internalization is profoundly synergistic. Further, the dimer of the present invention may also be synergistic when used with other CXCR4 pharmacophores.

A. Inflammation.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," Inflammation, 24(2): 141-155, (2000). Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group. Additionally, animal models for inflammatory bowel disease can also be used to assess the efficacy of the combination therapies of invention.

Animal models for asthma can also be used to assess the efficacy of the combination therapies of invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, J. Exp. Med. 186, 1737-1747).

B. Auto-Immune Disorders.

Animal models for autoimmune disorders can also be used to assess the efficacy of the combination therapies of invention. Animal models for autoimmune disorders such as type 1 diabetes, thyroid autoimmunity, systemic lupus eruthematosus, and glomerulonephritis have been developed. Further, any assays known to those skilled in the art can be used to evaluate the prophylactic and/or therapeutic utility of the combinatorial therapies disclosed herein for autoimmune and/or inflammatory diseases.

Animal models for autoimmune and/or intestinal inflammation can also be used to test the efficacy of the combination therapies of the invention. An example of one such model is the murine dextran sodium sulfate colitis model as described in Wirtz S. et al., "Chemically induced mouse models of intestinal inflammations" Nature Protocols 2, 541-546, (2007).

C. Cancer.

The anti-cancer activity of the therapies used in accordance with the present invention can also be determined by using various experimental animal models for the study of cancer such as the SCID mouse model or transgenic mice or nude mice with human xenografts, animal models, such as hamsters, rabbits, etc. known in the art and described in Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher), herein incorporated by reference in their entireties.

Toxicity and efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC 50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by a variety of methods known to the art, including by direct cell count, by detecting changes in transcriptional activity of known genes such as proto-oncogenes or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials. Further, any assays known to those skilled in the art can be used to evaluate the prophylactic and/or therapeutic utility of the combinatorial therapies disclosed herein for treatment or prevention of cancer, inflammatory disorder, or autoimmune disease.

D. HIV Infection

The Human Immunodeficiency Virus (HIV) infects millions of people globally. Cases are reported from nearly every country amounting to 40 million adults and children living with HIV/AIDS worldwide. In 2001, 5 million people were newly infected with HIV, and there were 3 million adult and child deaths due to HIV/AIDS. A full third of those people living with AIDS are aged 15-24 (World Health Organization, 2001).

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and, without the administration of antiviral agents, immunomodulators, or both, death may result.

While treatments for HIV/AIDS exist, the drugs currently used in treatment modalities exhibit numerous side effects, require prolonged treatment that often induces drug resistance, and do not result in complete eradication of the virus from the body. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage. Even with the current success of reverse transcriptase inhibitors, it has been found that HIV patients can become resistant to a single inhibitor.

Thus, it is desirable to develop compounds for use in combination with other known HIV treatments to further combat HIV infection and inhibit the replication of drug resistant strains of HIV.

In use, the locked dimer of the present invention may be administered in combination with one or more other compound having activity against HIV disease or HIV-related disease. By "HIV disease or HIV-related disease" we mean a disease state which is marked by HIV infection. Such disorders associated with HIV infection include, but are not limited to, AIDS, Kaposi's sarcoma, opportunistic infections such as those caused by *Pneumocystis carinii* and *Mycobacterium tuberculosis*; oral lesions, including thrush, hairy leukoplakia, and aphthous ulcers; generalized lymphadenopathy, shingles, thrombocytopenia, aseptic meningitis, and neurologic disease such as toxoplasmosis, cryptococcosis, CMV infection, primary CNS lymphoma, and HIV-associated dementia, peripheral neuropathies, seizures and myopathy.

Standard tissue culture models of HIV infection can be used to determine the efficacy of $CXCL12\alpha_2$ locked dimer as an HIV entry inhibitor in combination with current HIV entry inhibitors. Suitable therapeutic agents for use in combination with the compounds of the present invention include, but are not limited to, protease inhibitors, non-nucleoside reverse transcriptase inhibitors, nucleoside reverse transcriptase inhibitors, antiretroviral nucleosides, entry inhibitors as well as other anti-viral agents effective to inhibit or treat HIV infection. Further examples of suitable therapeutic agents include, but are not limited to, zidovudine, didanosine, stavudine, interferon, lamivudine, adefovir, nevirapine, delaviridine, loviride, saquinavir, indinavir and AZT. Other suitable therapeutic agents include, but are not limited to, antibiotics or other anti-viral agents, e.g., acyclovir. Other combination therapies known to those of skill in the art can be used in conjunction with the compositions and methods of the present invention.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference for all purposes.

It is understood that the invention is not confined to the specific reagents, formulations, reaction conditions, etc., herein illustrated and described, but embraces such modified forms thereof as come within the scope of the following claims.

REFERENCES

1. Allen et al. (2007). Annu Rev Immunol 25, 787-820.
2. Shirozu et al. (1995). Genomics 28, 495-500.
3. Doranz et al. (1999). J Virol 73, 2752-2761.
4. Nagasawa et al. (1994). Proc Natl Acad Sci USA 91, 2305-2309.
5. Nagasawa et al. (1996). Nature 382, 635-638.
6. Tachibana et al. (1998). Nature 393, 591-594.
7. Zou et al. (1998). Nature 393, 595-599.
8. Heidemann et al. (2004). Am J Physiol Gastrointest Liver Physiol 286, G1059-1068.
9. Bleul et al. (1996). Nature 382, 829-833.
10. Feng et al. (1996). Science 272, 872-877.
11. D'Souza et al. (1996). et al. Nat Med 2, 1293-1300.
12. D'Souzav et al. (2000). JAMA 284, 215-222.
13. Miedema et al. (1994). Immunol Rev 140, 35-72.

14. Mulle et al. (2001). Nature 410, 50-56.
15. Zlotnik, A. (2006). Int J Cancer 119, 2026-2029.
16. Veldkamp et al. (2006). J Mol Biol 359, 1400-1409.
17. Farzan et al. (2002). J Biol Chem 277, 29484-29489.
18. Farzan et al. (1999). Cell 96, 667-676.
19. Farzan et al. (2002). J Biol Chem 277, 40397-40402.
20. Seibert et al. (2002). Proc Natl Acad Sci USA 99, 11031-11036.
21. Fong et al. (2002). J Biol Chem 277, 19418-19423.
22. Babcock et al. (2003). J Biol Chem 278, 3378-3385.
23. Veldkamp et al. (2005). Protein Sci 14, 1071-1081.
24. Segers et al. (2007). Circulation 116, 1683-1692.
25. O'Boyle et al. (2008). Examination of the chemotaxis blockade by non-GAG-binding chemokine receptor agonists. In Keystone Conference on Chemokines and Chemokine Receptors. Keystone Symposia, Keystone Resort, Keystone, Co.
26. Vijayalakshmi et al. (1994). Protein Sci 3, 2254-2271.
27. Somers et al. (2000). Cell 103, 467-479.
28. Veldkamp et al. (2007). Protein Expr Purif 52, 202-209.
29. Fricker et al. (2006). Biochem Pharmacol 72, 588-596.
30. Milligan et al. (2007). Trends Pharmacol Sci 28, 615-620.
31. Chabre et al. (2005). Biochemistry 44, 9395-9403.
32. James et al. (2006). Nat Methods 3, 1001-1006.
33. El-Asmar et al. (2005). Mol Pharmacol 67, 460-469.
34. Springael et al. (2005). Cytokine Growth Factor Rev 16, 611-623.
35. Bouvier et al. (2007). Nat Methods 4, 3-4; author reply 4.
36. Rosenbaum et al. (2007). Science 318, 1266-1273.
37. Cherezov et al. (2007). Science 318, 1258-1265.
38. Crump et al. (1997). Embo J 16, 6996-7007.
39. Loetscher et al. (1998). J Biol Chem 273, 22279-22283.
40. Jin et al. (2007). J Biol Chem. September 21; 282(38): 27976-83.
41. Markley et al. (2003). Methods Biochem Anal 44, 89-113.
42. Peterson et al. (2006). J Mol Biol 363, 137-147.
43. Cornilescu et al. (1999). J Biomol NMR 13, 289-302.
44. Herrmann et al. (2002). J Mol Biol 319, 209-227.
45. Linge et al. (2003). Proteins 50, 496-506.
46. Ohnishi et al. (2000). J Interferon Cytokine Res 20, 691-700.
47. Princen et al. (2003). Cytometry 51A, 35-45.
48. Heveker et al. (1998). Curr Biol 8, 369-376.
49. Peterson et al. (2006). J Mol Biol 363, 813-822.
50. Williams et al. (1996). J Biol Chem 271, 9579-9586.
51. Leong et al. (1997). Protein Sci 6, 609-617.
52. Fernando et al. (2004). J Biol Chem 279, 36175-36178.
53. Rajarathnam et al. (2006). Biochemistry 45, 7882-7888.
54. Schnitzel et al. (1994). J Leukoc Biol 55, 763-770.
55. Moore, M. A. (2001). Bioessays 23, 674-676.
56. Murdoch, C. (2000). Immunol Rev 177, 175-184.
57. Liotta, L. A. (2001). Nature 410, 24-25.
58. Helbig et al. (2003). J Biol Chem 278, 21631-21638.
59. Cooper et al. (2003). Cancer 97, 739-747.
60. Taichman et al. (2002). Cancer Res 62, 1832-1837.
61. Zeelenberg, et al. (2003). Cancer Res 63, 3833-3839.
62. Moller et al. (2003). Leukemia 17, 203-210.
63. Murakami et al. (2002). Cancer Res 62, 7328-7334.
64. Payne et al. (2002). J Invest Dermatol 118, 915-922.
65. Delilbasi et al. (2004). Oral Oncol 40, 154-157.
66. Scotton et al. (2002). Cancer Res 62, 5930-5938.
67. Hall et al. (2003). Mol Endocrinol 17, 792-803.
68. Milliken et al. (2002). Clin Cancer Res 8, 1108-1114.
69. Burger et al. (2003). Oncogene 22, 8093-8101.
70. Phillips et al. (2003). Am J Respir Crit Care Med 167, 1676-1686.
71. Mori et al. (2004). Mol Cancer Ther 3, 29-37.
72. Gockel et al. (2007). Future Oncol 3, 119-122.
73. Zlotnik, A. (2006). Contrib Microbiol 13, 191-199.
74. Retz et al. (2005). Int J Cancer 114, 182-189.
75. Eisenhardt et al. (2005). Eur Urol 47, 111-117.
76. Wang et al. (2006). Cancer Metastasis Rev 25, 573-587
77. Burger, J. A. (2008) *Leuk Res.*
78. Burger et al. (2008) *Leukemia.*
79. Nervi et al. (2008) *Blood.*
80. Tavor et al. (2008) *Leukemia* 22, 2151-5158.
81. Azab et al. (2009) *Blood.*
82. Burger et al. (2006). Blood 107, 1761-1767.

We claim:

1. A method of treating blood cancer in a subject comprising administering to the subject a therapeutically effective amount of a composition comprising a $CXCL12\alpha_2$ locked dimer polypeptide, wherein the blood cancer cells express CXCR4.

2. The method of claim 1 wherein the subject is human.

3. A method of treating leukemia in a subject comprising administering to the subject a therapeutically effective amount of a composition comprising a $CXCL12\alpha_2$ locked dimer polypeptide, wherein the leukemia cells express CXCR4.

4. A method of inhibiting migration of cancer cells in a subject comprising administering to the subject a therapeutically effective amount of a composition comprising a $CXCL12\alpha_2$ locked dimer polypeptide, wherein the cancer cells express CXCR4.

5. The method of claim 4 wherein the cancer cells are selected from the group consisting of leukemia, lymphoma and myeloma.

6. A method of inhibiting migration of leukemia cells in a subject comprising administering to the subject a therapeutically effective amount of a composition comprising a $CXCL12\alpha_2$ locked dimer polypeptide, wherein the leukemia cells express CXCR4.

7. The method of claim 1 wherein the blood cancer is selected from the group consisting of leukemia, lymphoma and myeloma.

* * * * *

SEQUENCE LISTING

```
<160> NUMBER OF SEQ ID NOS: 2

<210> SEQ ID NO 1
<211> LENGTH: 68
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Cys Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Cys Leu Asn Lys
65

<210> SEQ ID NO 2
<211> LENGTH: 38
```

```
<212> TYPE: PRT
<213> ORGANISM: Homo sapiens

<400> SEQUENCE: 2

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Ala Phe Arg Glu Glu
            20                  25                  30

Asn Ala Asn Phe Asn Lys
            35
```